United States Patent
Altenberg et al.

(10) Patent No.: US 11,471,411 B2
(45) Date of Patent: Oct. 18, 2022

(54) POLYMER NANODISCS FOR BIOTECHNOLOGY AND MEDICAL APPLICATIONS

(71) Applicant: Texas Tech University System, Lubbock, TX (US)

(72) Inventors: Guillermo A. Altenberg, Lubbock, TX (US); Hongjun Liang, Lubbock, TX (US)

(73) Assignee: Texas Tech University System, Lubbock, TX (US)

(*) Notice: Subject to any disclaimer, the term of this patent is extended or adjusted under 35 U.S.C. 154(b) by 0 days.

(21) Appl. No.: 16/648,307

(22) PCT Filed: Sep. 18, 2018

(86) PCT No.: PCT/US2018/051538
§ 371 (c)(1),
(2) Date: Mar. 18, 2020

(87) PCT Pub. No.: WO2019/055996
PCT Pub. Date: Mar. 21, 2019

(65) Prior Publication Data
US 2020/0281855 A1 Sep. 10, 2020

Related U.S. Application Data

(60) Provisional application No. 62/559,706, filed on Sep. 18, 2017.

(51) Int. Cl.
*A61K 9/127* (2006.01)
*C08F 293/00* (2006.01)

(52) U.S. Cl.
CPC ........ *A61K 9/1274* (2013.01); *C08F 293/005* (2013.01); *C08F 2438/03* (2013.01)

(58) Field of Classification Search
CPC . A61K 9/1274; C08F 293/05; C08F 2438/03; C08F 8/34; C08F 8/44; C08F 8/02; C08F 222/08; C08F 8/32; C08F 8/40; C08F 293/005
See application file for complete search history.

(56) References Cited

PUBLICATIONS

Fiori et al., Polymer-Encased Polymer Nanodiscs with Improved Buffer Compatibility, Scientific Reports, Article No. 7432, pp. 1-10. (Year: 2017).*
Denisov et al., Chem Rev. Mar. 22; 117(6): 4669-4713. doi:10.1021/acs.chemrev.6b00690. (Year: 2017).*
Chawla, Udeep et al. "A Usual G-Protein-Coupled Receptor in Unusual Membranes" Angew Chem Int Ed Engl. Jan. 11, 2016; 55(2): 588-592.

(Continued)

*Primary Examiner* — Carlos A Azpuru
(74) *Attorney, Agent, or Firm* — Edwin S. Flores; Daniel J. Chalker; Chalker Flores, LLP

(57) ABSTRACT

The present invention includes compositions, methods, and methods of making and using a nanoscale discoidal membrane comprising: an amphiphilic membrane patch comprising self-assembled molecular amphiphiles capable of supporting one or more membrane proteins in the amphiphilic membrane patch; and one or more amphipathic scaffold macromolecules that encase the nanoscale discoidal membrane.

21 Claims, 4 Drawing Sheets

(56) References Cited

PUBLICATIONS

Fiori, Mariana C. et al. "Polymer-encaces nanodiscs with improved buffer compatibility" Scientific Reports, published online Aug. 7, 2017, vol. 7, Article No. 7432, pp. 1-10.
Lindhoud, S. et al. "SMA-SH: Modified Styrene-Maleic Acid Copolymer for Functionalization of Lipid Nanodiscs" Biomacromolecules, 2016, vol. 17, pp. 1516-1522.
International Search Report and Written Opinion PCT/2018/051538 [ISA AU] dated Feb. 4, 2019.

* cited by examiner

POLYMER NANODISCS FOR BIOTECHNOLOGY AND MEDICAL APPLICATIONS

CROSS-REFERENCE TO RELATED APPLICATIONS

This application is the National Stage of International Application No. PCT/US2018/051538, filed on Sep. 18, 2018 claiming the priority of U.S. Provisional Application No. 62/559,706, filed on Sep. 18, 2017, the content of each of which is incorporated by reference herein.

TECHNICAL FIELD

The present invention relates in general to the field of polymer membrane nanodiscs and membrane proteins.

BACKGROUND ART

Without limiting the scope of the invention, its background is described in connection with membrane proteins.

Membrane proteins (MPs) are encoded by 20 to 30% of the sequenced genomes, and are the targets of most pharmacological agents.[1,2] Mutations of MPs are associated with many disorders, including cystic fibrosis, cerebrovascular accidents, deafness, cardiac infarcts, and neurodegenerative diseases.[3-7] Understanding the structure and function of MPs is of great importance and frequently requires work with purified MPs reconstituted in a model membrane. Ideally, this membrane platform should mimic native biomembranes to maintain the structural and functional integrity of MPs, and be robust and reliable under a broad range of abiotic conditions in long term for methodology and technology development.

Liposome is a popular MP-supporting platform, but the fluidic and labile nature of lipid bilayers limits its utility.[8-13] In addition, the lack of MP orientation control is an inevitable setback to MP-mediated transport, and the secluded intraliposomal side constitutes a challenge to study MP functions that involve ligand binding and signal transduction. The relatively large size of liposome also complicates optical spectroscopy measurements due to light scattering. Lipid nanodisc (LND) emerges as a new MP-supporting platform that overcomes some of the limitations of liposomes.[14-17] LND represents a small discoidal lipid bilayer patch encased within two belt-like membrane scaffold proteins (MSPs) derived from apolipoprotein A1, a major component of serum high-density lipoprotein complexes.[15,18] The diameter of LNDs ranges from 8 to 16 nm, depending largely on the length of the MSPs. This size range displays sufficient flexibility to accommodate a variety of MPs.[14-17] The homogeneous and monodisperse nature, the ready accessibility to both extramembrane domains of reconstituted MPs, and low light scattering noises are some of the prominent advantages of LNDs for methodologies such as luminescence spectroscopy, solution NMR spectroscopy and single-particle cryo-electron microscopy (cryo-EM).[16,19-22] LNDs have also gained increasing interests as a novel drug targeting and delivery platform.[23-25] Despite the promise and progress empowered by LNDs, the inherent instability of lipid bilayers and their inescapable structural evolution during storage and shipment is problematic for the development of LND-based diagnostic and therapeutic products. Crosslinking, bonding with supporting substrates, and encapsulation have been exploited to improve the stability of lipid bilayers,[10-13] but these modifications will likely compromise the structure and function of the embedded MPs. However, despite the current excitement about SMALPs, their use is strictly limited by the incompatibility of SMA and SMALPs with low pH solutions and some cationic solutes. Therefore, a need remains for improved nanodiscs that operate at physiological conditions such as pH and the need of these proteins to interact with cations under physiological conditions.

SUMMARY OF INVENTION

In one embodiment, the present invention includes a nanoscale discoidal membrane comprising: an amphiphilic membrane patch comprising self-assembled molecular amphiphiles capable of supporting one or more membrane proteins in the amphiphilic membrane patch; and one or more amphipathic scaffold macromolecules that encase the nanoscale discoidal membrane. In one aspect, the nanoscale discoidal membrane further comprising one or more membrane proteins in the amphiphilic membrane patch. In another aspect, the amphipathic scaffold macromolecules are polymers comprising a styrene-maleic acid derivative repeating units that carry zero or nearly zero negative charges; and/or one or more membrane scaffold proteins. In another aspect, the membrane proteins stabilized in the amphiphilic membrane have a higher mechanical and chemical stability when compared to the same membrane protein in a liposome. In another aspect, the one or more membrane proteins are soluble at a pH<7.0. In another aspect, the one or more membrane proteins are soluble in the presence of cations. In another aspect, the one or more membrane proteins are adapted for the determination of acidification-induced rhodopsins spectral shifts, activation of ion channels such as KcsA, or measurement of ATPases. In another aspect, the one or more membrane proteins are rhodopsins, ion pumps, ATP-binding cassette proteins. In another aspect, the one or more membrane proteins are soluble in the presence of cations and a pH<7.0. In another aspect, the one or more membrane proteins are at least one of P-type, F-type, V-type, or ABC ATPases. In another aspect, the molecular amphiphiles comprise lipids isolated from cells. In another aspect, the molecular amphiphiles comprise synthetic lipids including amphiphilic block copolymers. In another aspect, the one or more membrane proteins is an integral membrane protein. In another aspect, the one or more membrane proteins shows minimal or no structural change upon storage at 4° C. or 20° C.

In another aspect, the amphiphilic block copolymers are either di-block copolymers in the form of AB or tri-block copolymers in the form of ABA, where A represents the hydrophilic polymer blocks including (but not limited to) Poly(4-vinyl-N-methylpyridine iodide) (P4MVP), Polyethylene glycol (PEG), Poly(N,N'-Dimethylacrylamide) (PDMA), Poly(2-methyloxazoline) (PMOXA), Poly(2-(dimethylamino)ethyl methacrylate) (PDMAEMA) etc., and B represents the hydrophobic polymer blocks including (but not limited to) Polybutadiene (PBD), Hydrogenated Polybutadiene (HPBD), Polydimethylsiloxane (PDMS), Poly(methyl acrylate) (PMA), Poly(methyl methacrylate) (PMMA), Polystyrene (PS) etc.

In another aspect, the self-assembled amphiphilic block copolymers has the exemplary formula:

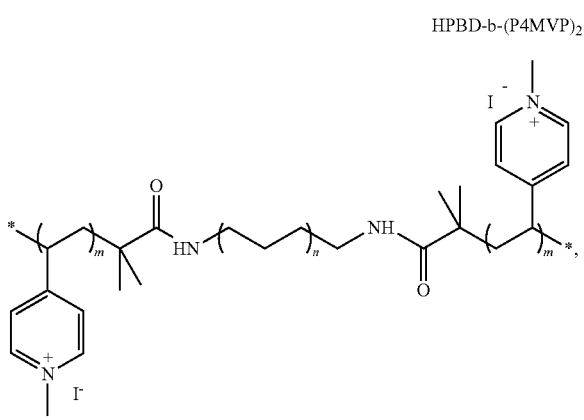

HPBD-b-(P4MVP)₂ wherein n is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 140, 145, 150, 155, 160, 165, 170, 175, 185, 190, 195, 200, or more, and m is 1 to 100.

In another aspect, the amphipathic scaffold macromolecules comprising a randomly polymerized styrene-maleic acid derivative repeating units that carry zero or nearly zero negative charges are the zwitterionic styrene-maleic acid polymers (zSMAs) with the structure:

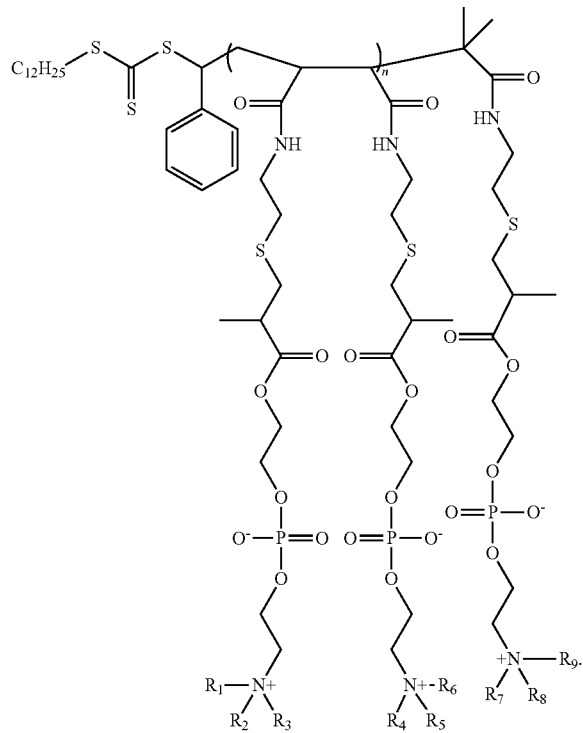

In another aspect, $R_1$, $R_2$, $R_3$, $R_4$, $R_5$, $R_6$, $R_7$, $R_8$, $R_9$ are selected from hydrogen; deuterium; a halogen group; a nitrile group; a nitro group; an imide group; an group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group including one or more of N, O, or S atoms; and wherein n is 1 to 200. In another aspect, n is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 140, 145, 150, 155, 160, 165, 170, 175, 185, 190, 195, 200, or more. In another aspect, the end groups of zSMA (e.g. $C_{12}H_{25}$—S—(C=S)—S—) shown in this structure are merely one example of the possible end groups of the zSMA, in this case they were introduced by reversible addition-fragmentation chain-transfer (RAFT) polymerization in the preparation of zSMA using S-1-dodecyl-S'-(α, α'-dimethyl-α"-acetic acid)trithiocarbonate (DATC) as the chain transfer agent. There are a wide variety of different possible end groups for zSMA should different RAFT chain transfer agents be chosen for the preparation of zSMA via RAFT polymerization, should the residue RAFT chain transfer moieties on zSMA be cleaved or converted to other groups, or should the zSMA be prepared via other polymerization methods, including but not limited to anionic polymerization, cationic polymerization, conventional free radical polymerization, or other types of controlled/living free radical polymerization such as atom transfer radical polymerization (ATRP), or nitroxide mediated polymerization (NMP).

In another embodiment, the present invention includes a method of making a nanoscale discoidal membrane comprising: obtaining an amphiphilic membrane patch comprising self-assembled molecular amphiphiles capable of supporting membrane proteins in the amphiphilic membrane patch; and adding one or more amphipathic scaffold macromolecules that encase the nanoscale discoidal membrane, wherein the membrane proteins stabilized in the amphiphilic membrane have a higher mechanical and chemical stability when compared to the same membrane protein in a liposome. In one aspect, the method further comprises adding one or more membrane proteins in the amphiphilic membrane patch. In another aspect, the one or more integral membrane proteins are soluble at a pH<7.0. In another aspect, the one or more integral membrane proteins are soluble in the presence of cations. In another aspect, the one or more integral membrane proteins are adapted for the determination of acidification-induced rhodopsins spectral shifts, activation of ion channels such as KcsA, or measurement of ATPases. In another aspect, the one or more integral membrane proteins are rhodopsins, ion pumps, ATP-binding cassette proteins. In another aspect, the one or more integral membrane proteins are at least one of P-type, F-type, V-type, or ABC ATPases. In another aspect, the amphiphiles comprise lipids isolated from cells. In another aspect, the amphiphiles comprise synthetic lipids including amphiphilic block copolymers.

In another aspect, the amphiphilic block copolymers are either di-block copolymers in the form of AB or tri-block copolymers in the form of ABA, where A represents the hydrophilic polymer blocks including (but not limited to) Poly(4-vinyl-N-methylpyridine iodide) (P4MVP), Polyethylene glycol (PEG), Poly(N,N'-Dimethylacrylamide) (PDMA), Poly(2-methyloxazoline) (PMOXA), Poly(2-(dimethylamino)ethyl methacrylate) (PDMAEMA) etc., and B represents the hydrophobic polymer blocks including (but not limited to) Polybutadiene (PBD), Hydrogenated Polybutadiene (HPBD), Polydimethylsiloxane (PDMS), Poly(methyl acrylate) (PMA), Poly(methyl methacrylate) (PMMA), Polystyrene (PS) etc.

In another aspect, the self-assembled amphiphilic block copolymers has the exemplary formula:

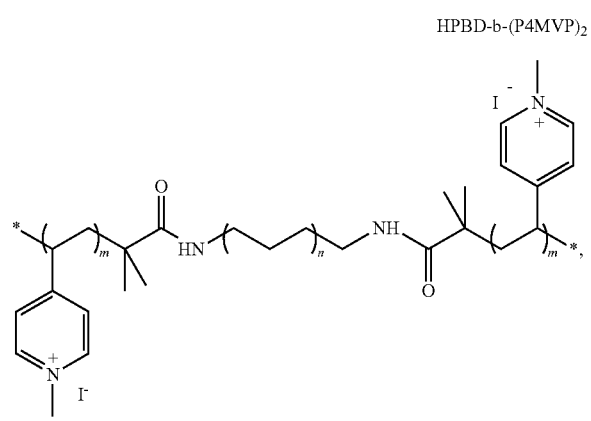

HPBD-b-(P4MVP)$_2$ wherein n is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 140, 145, 150, 155, 160, 165, 170, 175, 185, 190, 195, 200, or more, and m is 1 to 100.

In another aspect, the amphipathic scaffold macromolecules are zwitterionic polymers with styrene-maleic acid derivative repeating units and the structures:

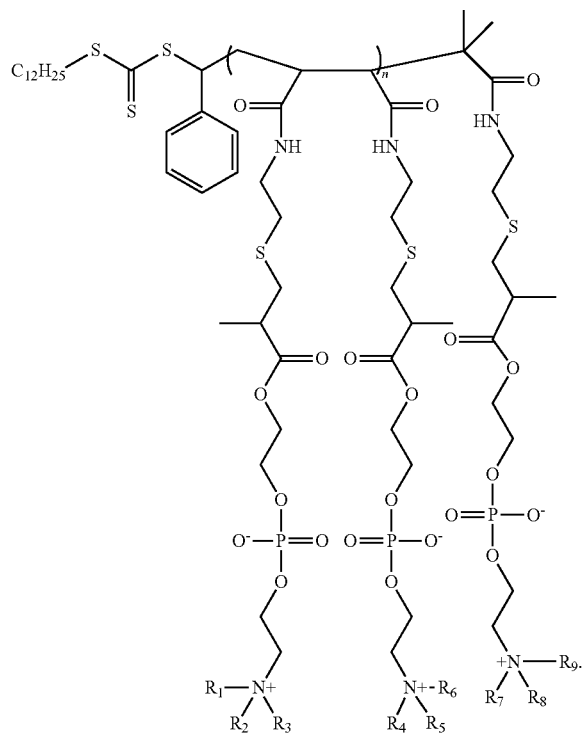

In another aspect, $R_1$, $R_2$, $R_3$, $R_4$, $R_5$, $R_6$, $R_7$, $R_8$, $R_9$ are selected from hydrogen; deuterium; a halogen group; a nitrile group; a nitro group; an imide group; an group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group including one or more of N, O, or S atoms; and wherein n is 1 to 200. In another aspect, n is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 140, 145, 150, 155, 160, 165, 170, 175, 185, 190, 195, 200, or more. In another aspect, the end groups of zSMA (e.g. $C_{12}H_{25}$—S—(C=S)—S—) shown in this structure are merely one example of the possible end groups of the zSMA, in this case they were introduced by reversible addition-fragmentation chain-transfer (RAFT) polymerization in the preparation of zSMA using S-1-dodecyl-S'-(α, α'-dimethyl-"-acetic acid)trithiocarbonate (DATC) as the chain transfer agent. There are a wide variety of different possible end groups for zSMA should different RAFT chain transfer agents be chosen for the preparation of zSMA via RAFT polymerization, should the residue RAFT chain transfer moieties on zSMA be cleaved or converted to other groups, or should the zSMA be prepared via other polymerization methods, including but not limited to anionic polymerization, cationic polymerization, conventional free radical polymerization, or other types of controlled/living free radical polymerization such as atom transfer radical polymerization (ATRP), or nitroxide mediated polymerization (NMP).

In yet another embodiment, the present invention includes a nanodisc comprising an amphiphilic block copolymer membrane patch comprised of a hydrophobic membrane-forming and hydrophilic membrane-surface blocks encased within one or more amphipathic scaffold macromolecules capable of stabilizing one or more membrane proteins. In one aspect, the membrane proteins are soluble at a pH<7.0. In another aspect, the membrane proteins are soluble in the presence of cations. In another aspect, the membrane proteins are adapted for the determination of acidification-induced rhodopsins spectral shifts, activation of ion channels (such as KcsA), or measurement of ATPases. In another aspect, the membrane proteins are rhodopsins, ion pumps, ATP-binding cassette proteins. In another aspect, the membrane proteins are soluble in the presence of cations and a pH<7.0. In another aspect, the membrane proteins are at least one of P-type, F-type, V-type, or ABC ATPases. In another aspect, the membrane proteins is an integral membrane protein.

In yet another embodiment, the present invention includes a method of making protein Polymer Nanodiscs (PNDs) comprising: dissolving a self-assembled molecular amphiphile selected from an amphiphilic HPBD-b-(P4MVP$_{28}$)$_2$ triblock copolymer (polymer), in a buffered aqueous solution; sonicating the buffered aqueous solution; freezing and thawing one or more times the sonicated buffered aqueous solution; combining zero, one or more membrane proteins with the polymer; and self-assembling the PNDs by adding a membrane scaffold protein to the membrane protein and the polymer.

In another aspect, the self-assembled P4MVP-HPBD-P4MVP amphiphilic block copolymers has the general formula:

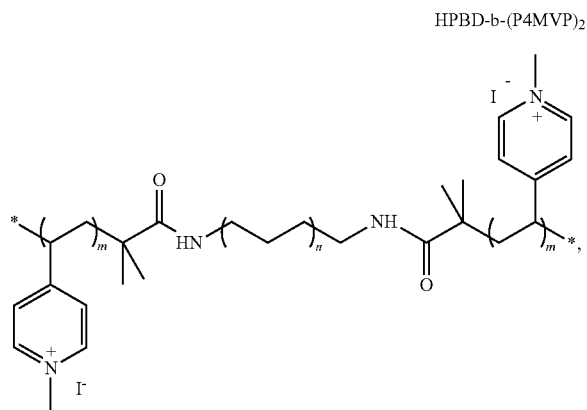

wherein n is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 140, 145, 150, 155, 160, 165, 170, 175, 185, 190, 195, 200, or more, and m is 1 to 100.

BRIEF DESCRIPTION OF DRAWINGS

For a more complete understanding of the features and advantages of the present invention, reference is now made to the detailed description of the invention along with the accompanying figures and in which:

FIG. 2A is a graph that shows SEC traces of HPBD (black; M$_n$=2,230 Da, PDI=1.14) and HPBD-b-(P4VP)$_2$ (red; M$_n$=8,690 Da, PDI=1.16). FIG. 2B is a graph and in insert that show DLS of self-assembled HPBD-b-(P4MVP)$_2$ in water showing the formation of polymersomes of different sizes (peak: ~86-nm diameter). The polymersomes can be directly observed under TEM (inset; scale bar: 50 nm).

FIG. 3A shows typical examples illustrating PNDs and LNDs hydrodynamic diameter distributions determined by DLS. FIG. 3B shows a summary of the average hydrodynamic diameter data showing means±SEM of PNDs (n=10), MsbA-PNDs (n=7), LNDs (n=7) and MsbA-LNDs (n=7). FIG. 3C shows absorption spectra of PNDs and the amphiphilic block copolymer itself in solution. FIG. 3D shows samples of a representative gel (16% SDS-PAGE) stained with Instant Blue (Expedeon) for protein detection. FIG. 3E shows typical SEC of PNDs revealing the co-existence of MsbA and the block copolymer membrane.

FIG. 5A shows typical examples illustrating PNDs and LNDs hydrodynamic diameter distributions determined by DLS. FIG. 5B shows the aggregation of PNDs and LNDs kept at 4° C. and 20° C., respectively, for 1 week as revealed by DLS measurements.

DESCRIPTION OF INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

CMC, critical micelle concentration; DLS, dynamic light scattering; EM, electron microscopy; GPCR, G-protein coupled receptor; HPBD, hydrogenated polybutadiene; IMAC, immobilized metal-affinity chromatography; LND, lipid nanodisc; MP, membrane protein; MSP, membrane scaffold protein; NMR, nuclear magnetic resonance; P4MVP, poly(4-vinyl-N-methylpyridine iodide); P4VP, poly(4-vinylpyridine); PBD, polybutadiene; PDMS, polydimethylsiloxane; PND, polymer nanodisc; PS, polystyrene; RAFT, reversible addition-fragmentation chain transfer; SEC, size-exclusion chromatography; TEM, transmission electron microscopy.

Figure 1:
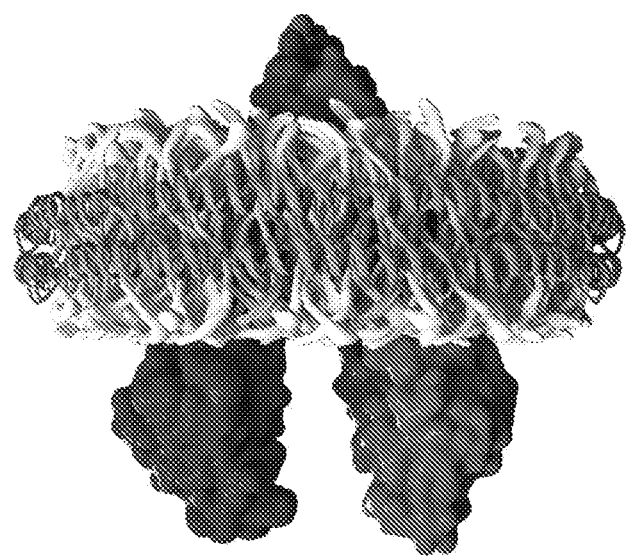
FIG. 1 is an illustration of PND with reconstituted MsbA. The amphiphilic block copolymer membrane patch comprised of hydrophobic membrane-forming (gold) and hydrophilic membrane-surface blocks (gray) is encased within two MSPs (green ribbon coils).

The present inventors disclose herein composition and methods of making polymer nanodisc (PND) that include a discoidal amphiphilic block copolymer membrane patch encased within membrane scaffold proteins (MSPs) as a new platform of improved stability that supports MPs (FIG. 1). The amphiphilic block copolymers can self-assemble in water spontaneously to form polymersomes, i.e., liposome-like polymer vesicles.[26, 27] In contrast to lipids, block copolymers have low critical micelle concentrations (CMCs) and much enhanced chemical and mechanical stability, as well as practically unlimited choices of chemical variations on individual repeating units. These advantages have prompted many explorative studies to adapt polymersomes as liposome-substitutes for supporting MPs[8, 28-35] or delivering pharmaceuticals.[36, 37] The present inventors demonstrate herein that in the presence of detergents and MSPs, a selective transition from polymersomes to PNDs occurs upon detergent removal, demonstrating a broadly applicable physical principle that guides the transition from vesicle to nanodisc.[38, 39] Using the bacterial ATP-binding cassette (ABC) transporter MsbA[21, 40-42] as a MP prototype, the present inventors show that reconstitution of individual MsbA dimer in PNDs is possible, and this reconstitution significantly improved the activity of MsbA compared to its detergent-solubilized form. The chemically and mechanically more stable PND shows negligible structural change upon storage at 4° C. or 20° C., in contrast to lipid nanodiscs (LNDs), which experiences time- and temperature-dependent aggregation.

This disclosure demonstrates PNDs as a new membrane protein (MP)-supporting platform with enhanced stability, which is critical for the development of nanodisc-based characterization methodologies and diagnostic or therapeutic applications. Likewise, the PNDs by themselves without embedded MPs are also useful platforms for diagnostic or therapeutic applications.

The disclosed invention includes a method to prepare a synthetic polymer membrane designed to replace the lipid bilayer in nanodiscs. The disclosed invention also encompasses a polymer nanodisc comprising the synthetic mimics of membrane scaffold proteins (MSPs), such as the polymeric styrene-maleic acid derivatives recently published by the inventors (Fiori M C, Jiang Y, Altenberg G A, and Liang H J, Sci. Rep., 7432 (7), 2017), as well as synthetic lipid replacements, to arrive at a completely synthetic nanodisc.

Lipid nanodiscs are playing increasingly important roles for studying the structure and function of membrane proteins. Development of lipid nanodiscs as membrane-protein-supporting platforms, or drug targeting and delivery vehicles in general, is undermined by the fluidic and labile nature of lipid bilayer itself. Here, the inventors developed novel polymer nanodisc, i.e., a discoidal amphiphilic block copolymer membrane patch encased within membrane scaffold proteins, as a novel two-dimensional nanomembrane that maintains the advantage of lipid nanodiscs while addressing its weakness. Using MsbA, a well-known bacterial ATP-binding cassette transporter as a membrane protein model, the inventors show that individual MsbA dimer can be reconstituted into the polymer nanodiscs in a functional state. As with lipid nanodiscs, reconstitution of detergent-solubilized MsbA into the polymer nanodiscs significantly enhances its activity. Importantly, in contrast to lipid nanodiscs that undergo time- and temperature-dependent structural changes, the polymer nanodiscs experience negligible structural evolution under similar environmental stresses, revealing a critically important property for the development of nanodisc-based characterization methodologies or biotechnologies. The higher mechanical and chemical stability of block copolymer membranes and their chemical versatility for adaptation opens new opportunities for applications built upon diverse membrane protein functions, or involved with drug targeting and delivery.

FIG. 1 is an illustration of polymer nanodiscs (PND) with reconstituted MsbA. The amphiphilic block copolymer membrane patch comprised of hydrophobic membrane-forming (gold, center ring portion) and hydrophilic membrane-surface blocks (gray, outer ring portion) is encased within two membrane scaffold proteins (MSPs) (green ribbon coils, coils surrounding the central portion). One reconstituted MsbA dimer (subunits in purple and blue) is also shown. This PND model is demonstrated herein below using spectroscopy and microscopy analysis.

The novel polymer nanodiscs (PND) of the present invention include a generally discoidal amphiphilic block copolymer membrane patch encased within MSPs as a new platform of improved stability that supports membrane proteins (MPs) (FIG. 1). Amphiphilic block copolymers can self-assemble in water spontaneously to form polymersomes, i.e., liposome-like polymer vesicles.[26, 27] In contrast to lipids, block copolymers have low critical micelle concentrations (CMCs) and much enhanced chemical and mechanical stability, as well as practically unlimited choices of chemical variations on individual repeating units. These advantages have prompted many explorative studies to adapt polymersomes as liposome-substitutes for supporting MPs[8, 28-35] or delivering pharmaceuticals.[36, 37] The present inventors demonstrate here, for the first time, that in the presence of detergents and MSPs, selective transition from polymersomes to PNDs occurs upon detergent removal, underlying a broadly applicable physical principle that guides the transition from vesicle to nanodisc.[38, 39] Using the bacterial ATP-binding cassette (ABC) transporter MsbA[21, 40-42] as a MP prototype, the inventors show that reconstitution of individual MsbA dimer in PNDs is possible, and this reconstitution significantly improved the activity of MsbA compared to its detergent-solubilized form. The chemically and mechanically more stable PND shows negligible structural change upon storage at 4° C. or 20° C., in contrast to LND which experiences time- and temperature-dependent aggregation. Thus, PNDs are a new MP-supporting platform with enhanced stability, which is critical for nanodisc-based characterization methodologies and diagnostic or therapeutic applications. Likewise, the PNDs by themselves without embedded MPs are also useful platforms for diagnostic or therapeutic applications.

Support of MPs in Amphiphilic Block Copolymer Membranes. While the roles of specific endogenous lipids on the function of some MPs have been established,[43-46] it has been recognized that a major role of lipids is related to their contribution to the bulk physicochemical properties of biomembranes, such as curvature, lateral pressure profile, and thickness.[47-51] In this context, it is not surprising to observe that a large number of detergent-solubilized MPs retain their functions after reconstitution in lipid bilayers of very simple compositions, suggesting that the specific endogenous lipids critical for these MPs, if exist, may be bound tightly to the MPs and survive the detergent solubilization and reconstitution steps.[44, 52-54] The non-exclusive partnership between MPs and native biomembranes opens up opportunities to study the structure and function of MPs in simple model membranes, including synthetic polymer membranes that mimic the physicochemical properties of biomembranes,[8, 28-35] and to develop MP-based biotechnology.[9, 55, 56] It should be noted that endogenous lipids can be still doped into the synthetic membranes when needed.[57, 58] Polydimethylsiloxane (PDMS)-based triblock copolymers membranes have been widely used to support MPs such as OmpF, aquaporin, ATP synthase, and potassium channel.[28-32] However, due to the low glass transition temperature of PDMS, these membranes are in a viscous fluid state at room temperature, which is undesirable for many biotechnological applications.

To address the membrane stability issue and to understand the role of membranes on defining MP functions, the inventors developed polybutadiene (PBD)- and polystyrene (PS)-based block copolymer membranes with systematically increasing membrane stability.[8, 33-35] The inventors showed that functional reconstitution of proteorhodopsin, a light-driven proton pump,[8, 33] bacterial reaction center, a light-driven electron-hole generator,[34] and bovine rhodopsin, a canonical prototype of G-protein coupled receptors (GPCRs)[35] into these membranes is possible. While the reaction center-mediated electron-transport kinetics appear insensitive to different membranes,[34] the proton-pumping photocycle of proteorhodopsin is allosterically slowed down as the membrane flexibility decreases.[8] Even glassy PS membranes with superior bulk-state stability can be tuned to bear sufficient chain-motion freedom at the nanoscale that rivals lipid bilayers to support the conformation changes of proteorhodopsin, underscoring the versatility of polymer membranes to support MPs with optimized stability and performance.[8] The versatility was also demonstrated by the discovery of a new activation mode for bovine rhodopsin, which was known to depend highly on endogenous lipids for activation, by revealing that the attractive charge interaction between the polymer membrane surface and the deprotonated Glu134 residue of the rhodopsin-conserved ERY sequence motif can be introduced to replace the role of native biomembranes by breaking the cytoplasmic "ionic lock" of rhodopsin to dock transducin.[35]

Synthesis and Characterization of an Amphiphilic Block Copolymer Membrane. As a model system to test the feasibility of PNDs, the inventors first used the hydroxyl-terminated, hydrogenated polybutadiene (HPBD-(OH)$_2$) that is commercially available (Krasol® HLBH-P 2000 from Cray Valley USA) as the building block to prepare well-defined triblock copolymer HPBD-b-(poly(4-vinylpyridine))$_2$ (HPBD-b-(P4VP)$_2$) via reversible addition-fragmentation chain transfer (RAFT) polymerization. The HPBD is more stable than PBD due to the lack of unsaturated bonds. The hydroxyl end groups of the HPBD were further converted to amines in order to form amide bonds with the P4VP blocks instead of the more labile ester bonds. The inventors then used the quaternization reaction to convert the P4VP blocks into hydrophilic poly(4-vinyl-N-methylpyridine iodide) (P4MVP). The reaction scheme to prepare the amphiphilic triblock copolymer HPBD-b-(P4MVP)$_2$ and its structural characterization is shown herein below. Both nuclear magnetic resonance (NMR) spectroscopy (FIGS. 6A-6D and FIGS. 7A-7B) and size-exclusion chromatography (SEC) analysis (FIG. 2A) confirmed the successful synthesis of well-defined HPBD-b-(P4VP$_{28}$)$_2$ with a small polydispersity index (PDI). The amphiphilic HPBD-b-(P4MVP$_{28}$)$_2$ self-assembles spontaneously in water to form polymersomes of different sizes, with a peak-intensity diameter of ~86 nm as determined by dynamic light scattering (DLS) (FIG. 2B). The formation of polymersomes was also confirmed by transmission electron microscopy (TEM) (FIG. 2B, inset).

Figure 2A:
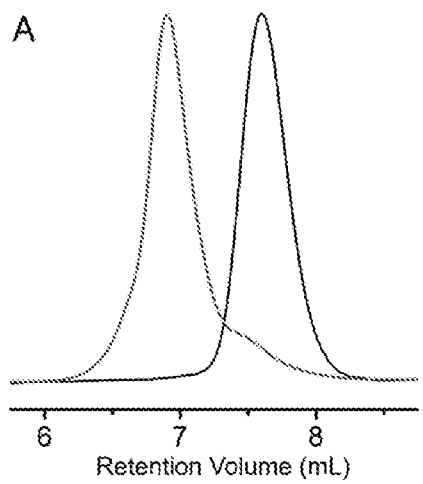
FIGS. 2A and 2B show well-defined amphiphilic block copolymer HPBD-b-(P4MVP)$_2$ self-assembled in water to form polymersomes.
Figure 2B:
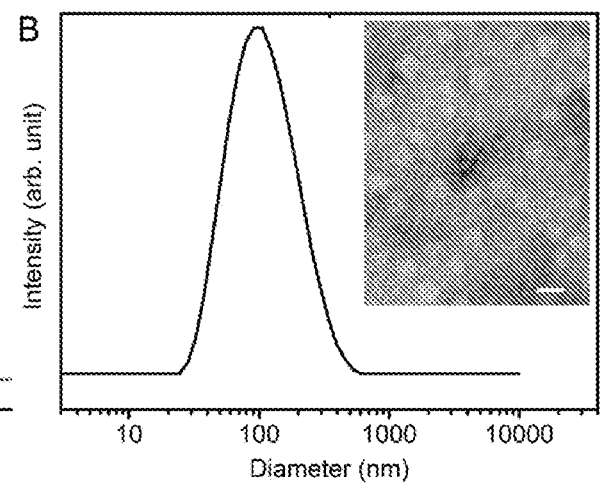

FIGS. 2A and 2B show well-defined amphiphilic block copolymer HPBD-b-(P4MVP$_{28}$)$_2$ self-assembled in water to form polymersomes. FIG. 2A is a graph that shows SEC traces of HPBD (black; $M_n$=2,230 Da, PDI=1.14) and HPBD-b-(P4VP$_{28}$)$_2$ (red; $M_n$=8,690 Da, PDI=1.16). FIG. 2B is a graph and in insert that show DLS of self-assembled HPBD-b-(P4MVP$_{28}$)$_2$ in water showing the formation of polymersomes of different sizes (peak: ~86-nm diameter). The polymersomes can be directly observed under TEM (inset; scale bar: 50 nm).

PND as a New Membrane Platform for MPs. To take advantage of the nanodisc platform[14-17, 23-25] while addressing the fluidic and labile nature of lipid bilayers, the inventors developed the PNDs disclosed herein and hypothesized that the transition from polymersomes to PNDs upon removal of detergent from a mixture of detergent, MSP, and amphiphilic block copolymers shares similar driving forces to those involved in the formation of LNDs. The inventors successfully developed a relatively simple and efficient protocol starting with a mixture of MSP1E3D1 and detergent-solubilized HPBD-b-(P4MVP$_{28}$)$_2$, followed by dilution of the detergent, and purification of PNDs by immobilized metal-affinity chromatography (IMAC) based on the affinity of the MSP poly-His tag for Ni$^{2+}$.

Figure 3A:
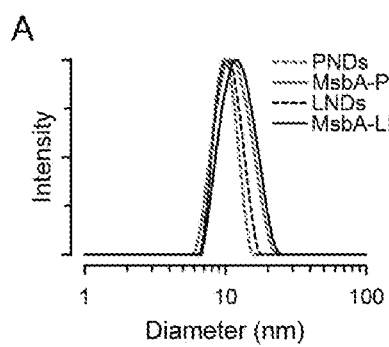
FIGS. 3A to 3E show the characterization of PNDs and their comparison with LNDs.
Figure 3B:
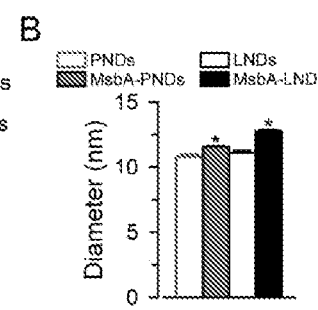
Figure 3C:
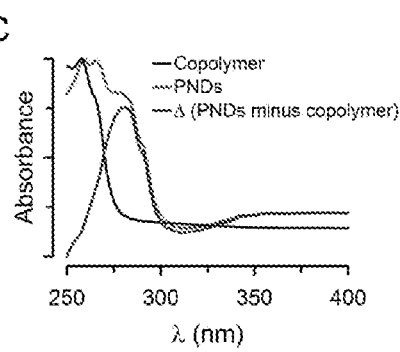
Figure 3D:
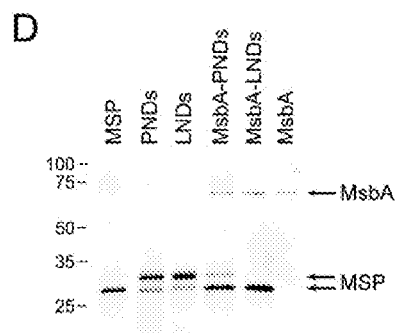
Figure 3E:
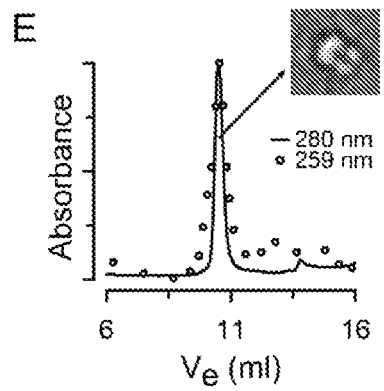

FIGS. 3A to 3E show the characterization of PNDs and their comparison with LNDs. FIG. 3A shows typical examples illustrating PNDs and LNDs hydrodynamic diameter distributions determined by DLS. FIG. 3B shows a summary of the average hydrodynamic diameter data showing means±SEM of PNDs (n=10), MsbA-PNDs (n=7), LNDs (n=7) and MsbA-LNDs (n=7). The asterisks denote P<0.002 vs. the corresponding MsbA-loaded nanodiscs. FIG. 3C shows absorption spectra of PNDs and the amphiphilic block copolymer itself in solution. Spectra are normalized to the corresponding peak value of the characteristic block copolymer absorption (i.e., $A_{259}$). The difference between the spectra is shown in blue. FIG. 3D shows samples of a representative gel (16% SDS-PAGE) stained with Instant Blue (Expedeon) for protein detection. Samples are indicated on top of the lanes. MsbA refers to MsbA T561C and MSP to MSP1E3D1. The 2 MSP arrows point to MSP1E3D1 with (top arrow) and without (bottom arrow) cleavage of the poly-His tag. The MSP in lane 1 and MsbA in lane 6 correspond to purified MSP1E3D1 and MsbA (DDM-solubilized MsbA T561C), respectively. The positions of molecular mass markers (in kDa) are indicated on the left. FIG. 3E shows typical SEC of PNDs revealing the co-existence of MsbA and the block copolymer membrane. The sample was run on a PL Aquagel-OH 50 column SEC column (see details below). The absorbance at 280 nm (line) was used to detect MSP and MsbA tryptophans, and the absorbance at 259 nm (circles) was used to follow the block copolymer membrane. Note that the block copolymer has an absorbance peak at 259 nm due to its pyridine moieties but no absorbance at 280 nm (FIG. 3C). Inset: an example of the cryo-EM of MsbA-loaded PND that clearly shows both the nanodisc and MsbA, resembling the inventors illustration of the PND (FIG. 1).

DLS studies (FIG. 3A) of the PNDs (dotted red trace) revealed fairly monodispersed nanoparticles with an average diameter of ~11 nm and a size distribution similar to that of LNDs (dotted black trace) prepared with the same MSP and E. coli polar lipid extract. The average data presented in FIG. 3B confirmed the similar sizes of PNDs (empty red bar) and LNDs (empty black bar). Also, the polydispersity index (PDI) calculated from the DLS data was similar for PNDs (8±1%, n=10) and LNDs (6±1%, n=7). FIG. 3C shows that the PNDs contain both copolymer and MSPs. The differential absorption spectra of empty PNDs (red) and the block copolymer itself in solution (black) clearly shows the tryptophan absorbance (blue) corresponding to the MSPs. The presence of MSPs in the PNDs was also illustrated by the MSPs in gels from PNDs stained for protein detection (FIG. 3D). Taken together, these data indicate that PNDs of fairly uniform size that contain MSPs and the copolymer can be produced using the inventors' protocol.

To test the reconstitution of MPs in PNDs, the inventors used the active mutant T561C of the bacterial MsbA, a frequently used model for structural and functional studies of ABC exporters.[21, 40-42] MsbA is a flippase that translocates lipid A, an endotoxin component, from the inner to the outer leaflet of the inner membrane of Gram-negative bacteria.[21, 42] To produce MsbA-loaded PNDs the inventors followed the protocol used for the formation of empty PNDs, but added detergent-solubilized MsbA to the MSP1E3D1/block copolymer mixture, and used a MSP1E3D1 without the poly-His tag. The tag of this MSP was removed by cleavage by TEV protease, and the untagged MSP was isolated as the flow through of an IMAC column. By using MsbA with a poly-His tag and untagged MSP the inventors could easily separate by IMAC the MsbA-loaded PNDs from empty ones. The incorporation of MsbA in the PNDs was confirmed by the increased hydrodynamic diameter determined by DLS (FIG. 3A, solid red vs. dotted red traces; and FIG. 3B, solid red vs. empty red bars), the presence of MsbA and MSP in gels of PNDs stained for protein detection (FIG. 3D), and the co-localization of protein (absorbance at 280 nm; $A_{280}$) and copolymer (absorbance at 259 nm; $A_{259}$) in high-resolution size-exclusion chromatograms (FIG. 3E). Using cryo-EM, the inventors also directly observed, for the first time, the MsbA-carrying PNDs (FIG. 3E, inset). As revealed by the gel in FIG. 3D, the proportion of MSP1E3D1 to MsbA was similar in PNDs (2.2±0.1; n=11) and LNDs (1.8±0.1; n=5), strongly suggesting that individual PNDs are encased within two copies of MSPs just like LNDs, as depicted in the PND model (FIG. 1).

Figure 4:
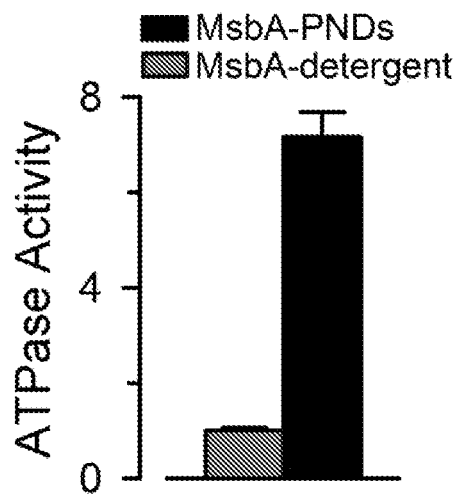
FIG. 4 is a graph that shows the ATPase activity of MsbA reconstituted in PNDs. The ATPase activity of purified MsbA T561C was measured at 37° C.

PND is a More Robust and Reliable MP-Supporting Platform than LND. Although the PND itself is made entirely by synthetic block copolymers without biological lipids, MsbA reconstituted in PNDs displays an ATPase activity several folds higher (~7×) than that of the detergent-solubilized MsbA (FIG. 4). This enhanced activity is similar to that reported previously for MsbA reconstituted in LNDs comprised of E. coli polar lipid extract.[21] Since no additional endogenous lipid was added during the reconstitution of detergent-solubilized MsbA into the PNDs, the inventors findings suggest that the physicochemical properties rather than specific chemical compositions of the membrane play an important role in supporting MsbA activity, and that it is possible to reconstitute functional MPs in PNDs.

FIG. 4 is a graph that shows the ATPase activity of MsbA reconstituted in PNDs. The ATPase activity of purified MsbA T561C was measured at 37° C. Values are presented as means±SEM relative to the activity in detergent (0.35±0.02 $s^{-1}$). The activity of MsbA in PNDs (n=12) was significantly higher (~7×) than that of MsbA in detergent (n=10; P<0.001).

Figure 5A:
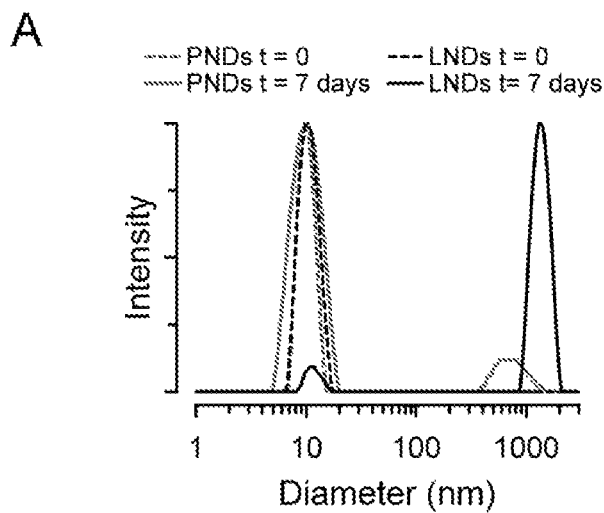
FIGS. 5A and 5B are graphs that show the stability of PNDs.
Figure 5B:
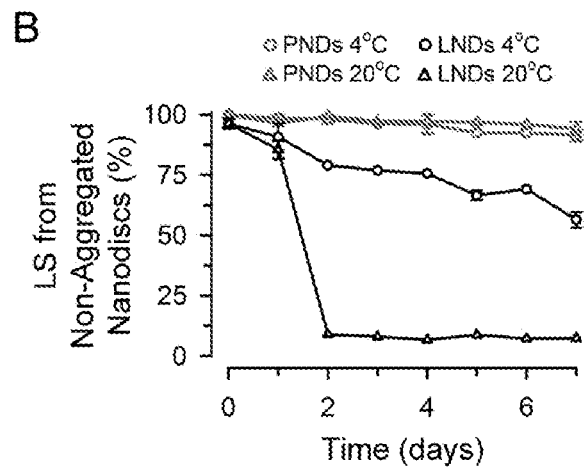

Given the fairly low gel-to-liquid transition temperature and fairly high CMC of many lipids, it has been recognized that the stability of LNDs depends highly on lipid compositions.[59-61] The instability of liposomes and LNDs is not particularly troublesome in research labs, as the user generally prepares and tests freshly made samples under well-controlled conditions (e.g., at 20° C. with short-term storage at 4° C.). However, it is a prohibitive challenge for applications under a broad range of harsher, abiotic conditions, such as those needed for remote collaborations that require sample exchange, or for the development of MP-based diagnostic and therapeutic products. When the inventors analyzed LNDs, the inventors observed their aggregation over time by light scattering measurements. Light scattering is sensitive to aggregation because of the steep dependency of scattering intensity on particle sizes. The examples in FIG. 5A illustrate that for LNDs (black) after 7 days stored at room temperature, most of the scattered light comes from large aggregated particles (1,000 to 2,000-nm diameter; solid trace) rather than the "fresh" LNDs (~11-nm diameter; dotted trace). In contrast, for PNDs stored under the same conditions (red), after 7 days most of the scattered light still comes from non-aggregated PNDs (solid trace) that have the same size as "fresh" PNDs (~11-nm diameter; dotted trace). The average data of multiple measurements quantitatively supporting increased stability of PNDs are depicted in FIG. 5B, which shows the percentage of scattered light coming from non-aggregated nanodiscs as a function of storage time and temperature. The LNDs show rapid aggregation in just 2 days when stored at 20° C. (black Δ). This aggregation behavior is alleviated when stored at 4° C. (black ○) but still significant. In contrast, the PNDs show negligible aggregation when stored at either 4° C. or 20° C. for 1 week. These surprising results show that PND is a significantly more robust and reliable platform than LND.

FIGS. 5A and 5B are graphs that show the stability of PNDs. FIG. 5A shows typical examples illustrating PNDs and LNDs hydrodynamic diameter distributions determined by DLS. FIG. 5B shows the aggregation of PNDs and LNDs kept at 4° C. and 20° C., respectively, for 1 week as revealed by DLS measurements. The figure shows the percentage of light scattered (LS) by nanodiscs consisting of a monodisperse population of 11-nm diameter assessed from size-intensity distributions such as those shown in FIG. 5A. Data are means±SEM of PNDs of 3 independent experiments in all conditions, except for PNDs and LNDs at t=0 (n=10 and 7, respectively), and PNDs at 20° C. in days 6 and 7, where n=1 and 2, respectively, and the single measurement and average are reported. SEMs smaller than the symbols are not shown. Differences between PNDs and LNDs were statistically significant (P<0.001) from day 2 onwards.

In summary, the inventors have developed and prepared novel PNDs comprised of well-defined amphiphilic block copolymer membranes to address the inherent limitation of LNDs. Using MsbA as a MP prototype, the inventors demonstrated that reconstitution of detergent-solubilized MsbA in the PNDs increases its activity, similar to that observed for the reconstitution of MsbA in LNDs. An important difference between PNDs and LNDs lies in their stability: unlike LNDs that aggregate significantly in a short time, PNDs show negligible time- and temperature-dependent structural evolution. PNDs are therefore better suited for applications that need survive a broad range of abiotic conditions in long term. Due to the higher mechanical and chemical stability of block copolymer membranes and their chemical versatility for adaptation, such as variation of membrane thickness and moduli, interfacing with supporting substrates, adding labels or specific recognition groups, to name a few, and the advantages of nanodiscs over other membrane platforms, the development of PNDs could have a powerful impact on biotechnology and biomedical applications built upon diverse MP functions or involved with drug targeting and delivery.

Expression and Purification of the MSP1E3D1. MSP1E3D1 was expressed in the E. coli strain BL21 DE3-RILP (Agilent Technologies) transformed with the plasmid pMSP1E3D1 (Addgene). Expression was induced at $OD_{600}$~1 with 1 mM isopropyl-β-D-thiogalactopyranoside and the cells were harvested after growing for 2 h at 37° C. MSP1E3D1 was purified by IMAC using Ni-NTA agarose beads (Qiagen), as described previously.[14, 21] For some experiments, the poly-His tag of the MSP was removed by digestion with TEV protease and the non-tagged MSP was isolated as the flow through from a column packed with Ni-NTA.[21, 62] Protein concentration was determined from the absorbance at 280 nm ($A_{280}$) and purity was estimated at >95% from SDS-PAGE gels stained with Instant Blue (Expedeon).

MsbA Expression, Purification, and Activity Assay. MsbA T561C (an active mutant that the inventors have studied extensively)[21, 42] was expressed and purified as previously described.[21, 42] Briefly, MsbA T561C expressed in BL21 DE3-RILP E. coli (Agilent Technologies) was solubilized from membranes with n-dodecyl-β-D-maltopyranoside (DDM; Inalco Pharmaceuticals), and purified by IMAC (Talon Superflow; Clontech) followed by SEC using a Bio-scale Mini Bio-Gel P-6 DC (Bio-Rad Laboratories)

equilibrated with 100 mM NaCl, 20 mM Tris/HCl, pH 7.5, with 0.065% DDM, 0.04% sodium cholate, 15% glycerol and 0.2 mM TCEP. Purified MsbA T561C was stored at −80° C. until use. As for MSP, protein concentration was determined from the $A_{280}$ and purity was estimated at >95% from SDS-PAGE gels stained with Instant Blue (Expedeon). ATPase activity was measured as described,[21, 42, 63] using a variant of the ATPase linked assay.

Production of Lipid Nanodiscs (LNDs). LNDs were assembled following a published protocol.[14, 21] E. coli polar lipid extract in chloroform (Avanti Polar Lipids) was dried overnight, reconstituted in nanodisc buffer (100 mM NaCl, 20 mM Tris/HCl, pH 7.5, 0.1 mM TCEP) with 100 mM sodium cholate and sonicated for several minutes. For the formation of LNDs the inventors used an MSP:lipid molar ratio of 1:100, and for the MsbA-loaded LNDs (MsbA-LNDs) the inventors used an MsbA:MSP molar ratio of 1:6. The mix was incubated for 1 h at 4° C. with gently rotation, and the self-assembly process was initiated upon detergent removal by incubation at 4° C. overnight with Biobeads SM-2 (Bio-Rad Laboratories). The LNDs were purified by SEC using a Superdex 200 Increase 10/300 column (GE Healthcare) equilibrated in nanodisc buffer, with a flow of 0.5 ml/min, and collection of 1-ml fractions for isolation of relevant peaks used in the studies. MsbA and MSP concentrations in the LNDs samples were estimated in SDS-PAGE gels stained with Instant Blue (Expedeon), using known amounts of purified MsbA and MSP as standards.

Production of Polymer Nanodiscs (PNDs). The amphiphilic HPBD-b-(P4MVP$_{28}$)$_2$ triblock copolymer was dissolved in 100 mM NaCl, 20 mM Tris/HCl, pH 7.5, with 80 mM n-octyl-β-D-glucopyranoside (OG; Anatrace) to a final concentration of 40 mg/ml (~2.5 mM). The solution was sonicated 3 times for 10 min each, and was flash-frozen in liquid $N_2$ and thawed on ice once. For the formation of PNDs, MSP1E3D1 was combined with the polymer at a MSP:copolymer molar ratio of 1:10, and the mix was incubated for 1 h at 4° C. with gentle rotation. For the production of MsbA-loaded PNDs, the inventors used a MSP:MsbA molar ratio of 6:1. After incubation of MsbA with the copolymer at 4° C., with gentle rotation for 10 min, MSP (without poly-His tag) was added. Self-assembly of PNDs was initiated by reducing the concentration of detergent by a 20-fold dilution with the same buffer, but without OG, and the mix was incubated overnight with Ni-NTA beads previously washed in the same buffer, at 4° C., with gentle rotation. The sample was then loaded onto a column, washed with 3 column volumes of 200 mM NaCl, 20 mM Tris/HCl, pH 7.5, with 5 mM imidazole, followed by 3 column volumes of the same buffer, but with the addition of 0.05% DDM. The PNDs were eluted using 3 column volumes of 200 mM NaCl, 20 mM Tris/HCl, pH 7.5, and 300 mM imidazole, without DDM. The presence of polymer in the elution fractions was determined by the absorbance at 259 nm ($A_{259}$) and that of MSP and MsbA by staining 16% gels (SDS-PAGE) with Instant Blue (Expedeon). The samples were analyzed by SEC using a PL Aquagel-OH 50 column (Agilent Technologies) equilibrated with 200 mM NaCl, 20 mM Tris/HCl, pH 7.5. The flow rate was set at 0.5 ml/min and 1-ml fractions containing PNDs were collected for the studies. The use of dilution to initiate the formation of PNDs was chosen because the copolymer was adsorbed by the Bio-Beads. The addition of DDM during the second wash was an effective and simple way to remove copolymer associated with PNDs, which accounted for a broader size distribution and apparently larger PNDs. DDM was not present after the wash.

Estimation of Nanoparticle Size and Size Distribution by DLS. DLS experiments were performed at 22° C. on a Zetasizer Nano ZSP (Malvern Instruments), using 40-μl microcuvettes. For the standard measurements the samples were centrifuged at 250,000 g for 20 min and the supernatant was used for the DLS measurements. To follow stability over time, the samples were centrifuged only at t=0. For each sample, measurements were repeated at least 3 times, with each being a 15-scan average (each ~15-s long). Size-intensity distributions were generated using the Zetasizer software version 7.11, and were analyzed using the protein analysis distribution.

Electron Microscopy and Image Processing of Polymersomes and PNDs. The morphology of polymersomes was characterized on a Hitachi H-8100 electron microscope equipped with an AMT digital side mount camera and operated at an accelerating voltage of 75 kV. The polymersomes were stained with 1% uranyl acetate on the TEM grid immediately before taking measurements. To observe PNDs serial dilutions of the sample were made and stained with uranyl formate as described,[64] using sample buffer (200 mM NaCl, 20 mM Tris/HCl pH 7.5) instead of water for the washes. Specimens were then imaged in a Tecnai 12 electron microscope (FEI Company, Hillsboro, Oreg.) equipped with a Lab6 electron source and operated at 120 kV. Micrographs were automatically collected under low dose conditions using EPU (FEI Company, Hillsboro, Oreg.) at a nominal magnification of 67000×. Under-focused images (1 to 3 μm) were recorded on a US4000 CCD camera (Gatan, Pleasanton, Calif.) with a pixel size at the specimen level of 1.77 Å. The contrast transfer function (CTF) of the images was determined using ctffind4.[65] Images were selected based on the following criteria: visual assessment of particle dispersion, quality of stain and background, low astigmatism; and amplitude of signal and correlation with the expected CTF in the frequency range of 50 to 10 Å. All further processing was performed within the framework of EMAN 2.12.[66] Particles were extracted with a box size of 150 pixels, CTF corrected and pooled in a set. Reference free classification of down sampled and low pass filtered (16 Å) images was used to eliminate "bad" particles and false positives resulted in a "cleaned" dataset. This set was subject to a second round of classification.

Data Presentation and Statistics. Data are shown as means±SEM, and statistical comparisons were performed by the Student's t test for unpaired data, or one-way analysis of variance, as appropriate. P<0.05 in a two-tail analysis was considered significant. The number of experiments (n) corresponds to independent measurements from at least three different preparations.

The 4-vinylpyridine (4VP; inhibited with 100 ppm of hydroquinone) was purchased from Sigma Aldrich, and purified by passing through a basic $Al_2O_3$ column before use. The 1,1'-azobis(cyclohexanecarbonitrile) (ACHN) and azobisisobutyronitrile (AIBN), also purchased from Sigma Aldrich, were re-crystallized from methanol twice before use. Hydrogenated hydroxyl-terminated polybutadiene, Krasol® HLBH-P 2000 (HPBD-(OH)$_2$; $M_n$~2,100 Da as indicated by the manufacturer) was a gift from Cray Valley USA, and was used as received. Methanesulfonyl chloride, N,N'-dicyclohexylcarbodiimide (DCC), 4-dimethylamino pyridine (DMAP), 1-ethylpiperidinium hypophoshite (EPHP) and methyl iodide were purchased from Sigma Aldrich, and were used as received. S-1-dodecyl-S'-(α,α'-dimethyl-α"-acetic acid)trithiocarbonate (DATC) was synthesized according literature. Lai, J. T.; Filla, D.; Shea, R. Functional polymers from novel carboxyl-terminated trithiocarbonates as highly efficient RAFT agents. Macromolecules 2002, 35, 6754-6756. All other chemicals and solvents were obtained from Aldrich and were used as received.

The chemical structures of polymers were characterized by $^1$H NMR (Jeol 400 MHz liquid-state NMR spectrometer), and the polymer size distribution was assessed by size-exclusion chromatography (SEC). SEC was performed on an Agilent 1260 HPLC system equipped with Wyatt Optilab T-rEX refractive index and a Wyatt MiniDAWN TREOS multi-angle light scattering detectors, using an Agilent PLgel 5 μm MIXED-D column (300×7.5 mm). The system was equilibrated with a mixture of DMF/THF=1/3 (v/v) and run at 0.5 ml/min at 20° C.

Synthesis of the Amphiphilic Block Copolymer HPBD-b-(P4MVP)$_2$ Synthesis of HPBD-(NH$_2$)$_2$. The inventors first converted the HPBD-(OH)$_2$ into HPBD-(NH$_2$)$_2$ following a previously reported method, as illustrated in Scheme 1 for the preparation of amide-bonded HPBD-b-(P4MVP)$_2$ that forms stable polymersomes. Chawla, U.; Jiang, Y. J.; Zheng, W.; Kuang, L. J.; Perera, S. M. D. C.; Pitman, M. C.; Brown, M. F.; Liang, H. J. A Usual G-Protein-Coupled Receptor in Unusual Membranes. Angew. Chem. Int. Ed. 2016, 55, 588-592. Briefly, methanesulfonyl chloride (4.33 g, 37.8 mmol) and 20 mL anhydrous THF were added to a 200-mL round-bottom flask, and the mixture was placed in an ice bath. To this, the present inventors added a mixture of triethylamine (3.82 g, 37.8 mmol) and HPBD-(OH)$_2$ (10.0 g, 9.50 mmol —OH) in 80 mL anhydrous THF was added dropwise. After 24 h the reaction solution was filtered to remove the insoluble triethylamine hydrochloride, and then precipitated into 10-fold methanol twice. The product HPBD-(OMs)$_2$ was collected by centrifugation (6,000 g for 5 min) and dried under vacuum. The purified HPBD-(OMs)$_2$ (5.0 g, 2.2 mmol) was subsequently dissolved in 60 mL THF and transferred into a Teflon container. After addition of 15 mL of a 28% ammonia aqueous solution under vigorously stirring the lid was tightly sealed and the mixture was stirred at 70° C. for three days. Ammonia was then allowed to evaporate by air flow in a fume hood. NaOH was then added dropwise from a 5 M solution until the pH reached 13, and the mixture was stirred for 1 h. The concentrated solution was precipitated into 10-fold of methanol, the solid was re-dissolved by dichloromethane, and washed with Millipore water three times. After dehydration with anhydrous MgSO$_4$, the solution was concentrated and precipitated into methanol twice. The product was dried under vacuum and characterized by $^1$H NMR.

Scheme 1. Synthesis of HPBD-(NH$_2$)$_2$ and HPBD-(DATC)$_2$

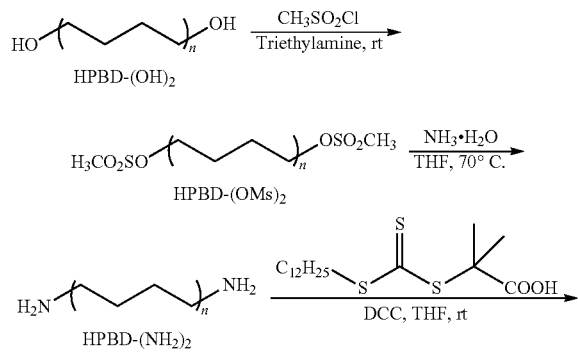

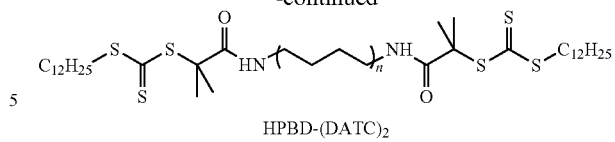

HPBD-(DATC)$_2$

Synthesis of macro-chain transfer agent (macro-CTA) HPBD-(DATC)$_2$. In order to synthesize HPBD-b-Poly(1-methyl-4-vinylpyridine)$_2$, i.e., HPBD-b-(P4MVP)$_2$ via reversible addition-fragmentation chain transfer (RAFT) polymerization, we first prepared macro-CTA HPBD-(DATC)$_2$ by reacting HPBD-(NH$_2$)$_2$ with DATC via DCC coupled amide formation, as shown in Scheme 1. Briefly, DCC (2.06 g, 10 mmol) and DATC (3.65 g, 10 mmol) were dissolved in 30 mL of anhydrous dichloromethane in a 100-mL flask. HPBD-(NH$_2$)$_2$ (1.0 g, 0.93 mmol —NH$_2$) was dissolved in 50 mL anhydrous dichloromethane and added to the flask dropwise. The mixture was stirred at room temperature for two days. After that, the insoluble solid was filtered away and the solution was concentrated in a rotary evaporator and precipitated into methanol three times. The product HPBD-(DATC)$_2$ was collected by centrifugation, dried under vacuum and characterized by $^1$H NMR.

Synthesis of the HPBD-b-(P4MVP)$_2$ amphiphilic triblock copolymer by RAFT polymerization. The HPBD-b-(P4VP)$_2$ triblock copolymer was synthesized by RAFT polymerization with HPBD-(DATC)$_2$ as the macro-CTA and AIBN as initiator, as shown in Scheme 2. In a typical run, HPBD-(DATC)$_2$ (0.2 g, 0.13 mmol DTAC), 4VP (0.76 g, 7.2 mmol) and AIBN (3.0 mg, 0.018 mmol) were dissolved in 1.7 mL THF in a 10-mL Schlenk flask equipped with a magnetic stir bar. After degassing by three freeze-pump-thaw cycles, the flask was immersed in a 60° C.-oil bath. After a predetermined time, the mixture was quenched by liquid nitrogen and precipitated into 10-fold hexanes twice. The product was collected by centrifugation, dried under vacuum and characterized by $^1$H NMR.

The hydrocarbon tail of the macro-CTA was subsequently removed by a reduction reaction, with 1-ethylpiperidinium hypophoshite (EPHP) as the reducing agent. In a typical run, HPBD-b-(P4VP$_{28}$-CTA)$_2$ (0.3 g, 0.034 mmol), EPHP (36 mg, 0.2 mmol) and ACHN (9.8 mg, 0.04 mmol) were dissolved in 6 mL DMF in a 10-mL Schlenk flask equipped with a magnetic stir bar. The mixture was degassed by three freeze-pump-thaw cycles and the flask was immersed in a 110° C.-oil bath for 4 h. The solution was then precipitated into an excess of diethyl ether. The precipitate was re-dissolved by dichloromethane, and washed with Millipore water three times. After dehydration with anhydrous MgSO$_4$, the solution was concentrated and precipitated into hexanes.

To obtain the amphiphilic triblock copolymer, HPBD-b-(P4VP$_{28}$)$_2$ was allowed to react with an excess of iodomethane in DMF at 45° C. for 24 h. The mixture was precipitated in 10-fold diethyl ether, and the product was dried in a vacuum oven overnight and characterized by $^1$H NMR.

Scheme 2. Synthesis of the amphiphilic triblock copolymer HPBD-b-(P4MVP)$_2$ by RAFT polymerization.

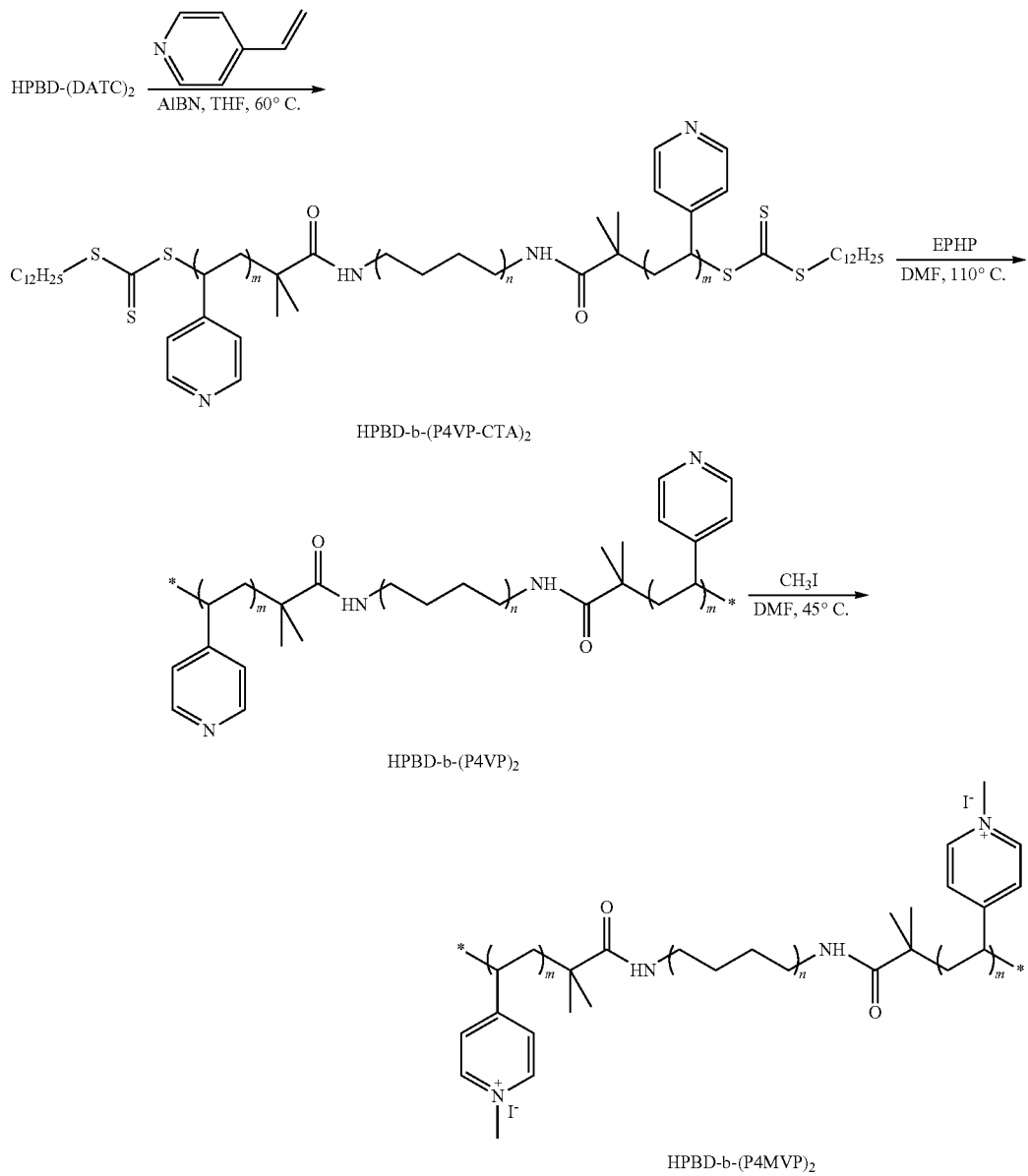

Figure 6A:
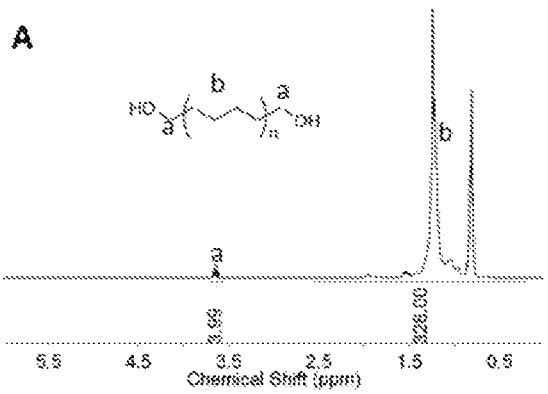
FIG. 6A to 6D are NMR spectra of (FIG. 6A) HPBD-(OH)$_2$, (FIG. 6B) HPBD-(OMs)$_2$, (FIG. 6C) HPBD-(NH$_2$)$_2$, and (FIG. 6D) HPBD-(DATC)$_2$. All spectra were measured in CDCl$_3$.
Figure 6B:
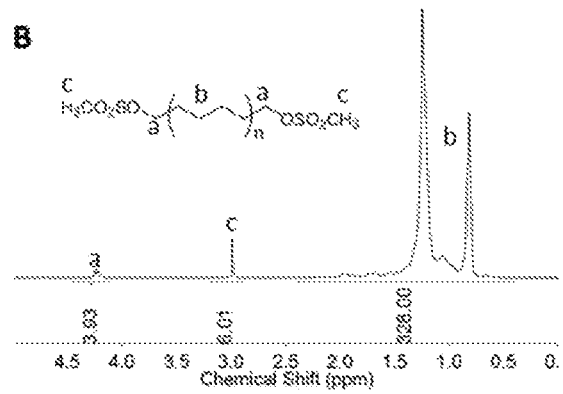
Figure 6C:
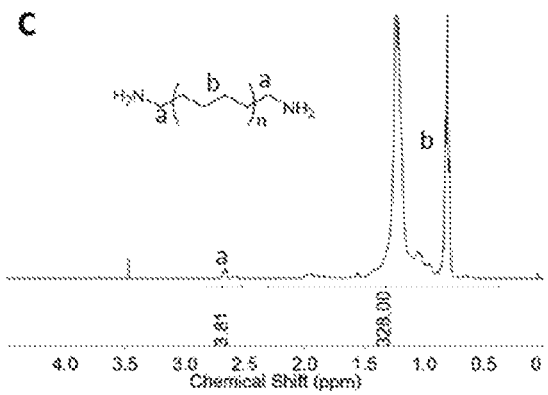

Synthesis of HPBD-(NH$_2$)$_2$ and HPBD$_2$-(DATC)$_2$. HPBD-(OMs)$_2$ was first synthesized in order to convert HPBD-(OH)$_2$ to HPBD-(NH$_2$)$_2$. The structures of HPBD-(OH)$_2$, HPBD-(OMs)$_2$, and HPBD-(NH$_2$)$_2$ were characterized by $^1$H NMR, as shown in FIG. 6A-C, respectively.

For HPBD-(OH)$_2$, both terminal hydroxyl groups were assumed to be bonded with —CH$_2$—. When the number of this methylene proton (a, FIG. 6A) was set to 4, there were 328 protons from the backbone. Since each monomer has 8 protons (b, FIG. 6A) and a formula weight of 56 Da, the actual molecular weight of HPBD-(OH)$_2$ was calculated to be 2,300 Da ($M_n$), which is slightly larger than the molecular weight ($M_n$=2,100 Da) indicated by the manufacturer. This NMR-derived molecular weight is in good agreement with that obtained by SEC-MALS measurements, which reports the absolute molecular weight. For HPBD-(OH)$_2$, the MALS analysis reported a $M_w$=2,540 and $M_n$=2,230 Da, with a polydispersity index (PDI) of 1.14 (FIGS. 2A and 2B). Consequently, the inventors used the 328 protons to account for all protons in the backbone of HPBD when we calculated the composition of other polymer products derived from HPBD-(OH)$_2$ using NMR.

For HPBD-(OMs)$_2$, when the integration of proton b was set to 328, there were 6 protons from the end methyl group (c, FIG. 6B), indicating that nearly 100% of hydroxyl groups have been reacted with methanesulfonyl chloride. After aminolysis of HPBD-(OMs)$_2$ the number of protons immediate next to —NH$_2$ (proton a in FIG. 6C) changed to 3.81, suggesting that >95% of —OH groups have converted to —NH$_2$.

Figure 6D:
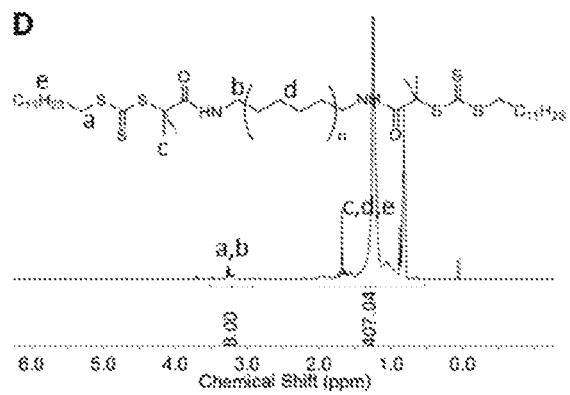

The HPBD-(NH$_2$)$_2$ was then reacted with DATC via DCC coupled amide formation and the NMR spectrum of the product is shown in FIG. 6D. Protons a and b have overlapping chemical shift and the total number was set to 8, assuming 100% functionalization of —$NH_2$ to graft DATC. Consequently, a total of 407 protons were calculated for protons c, d, and e, a value slightly larger than the expected number (i.e., 386). The overestimation (i.e., extra 21 protons, ~5% of the total) suggests that a very small portion of —$NH_2$ groups have not been functionalized with DATC.

FIG. 6A to 6D are NMR spectra of (FIG. 6A) HPBD-$(OH)_2$, (FIG. 6B) HPBD-$(OMs)_2$, (FIG. 6C) HPBD-$(NH_2)_2$, and (FIG. 6D) HPBD-$(DATC)_2$. All spectra were measured in $CDCl_3$.

Synthesis of the amphiphilic triblock copolymer HPBD-$(P4MVP)_2$. The inventors used HPBD-$(DATC)_2$ as the macro-CTA for the RAFT polymerization of HPBD-b-$(P4VP)_2$, and characterized the product by NMR (FIG. 7A) and SEC-MALS. When proton c was set to 4, there were 110 protons from proton a and 112 protons from proton b, indicating that the average degree of polymerization (DP) of each P4VP block was 28 units. The calculated molecular weight ($M_n$) of the block copolymer based on this DP was 8,910 Da, which is very similar to the absolute molecular weight measured by SEC-MALS (FIG. 2). The MALS analysis gave a $M_w$ of 10,090 Da, a $M_n$ of 8,690 Da, and a PDI of 1.16. The low PDI suggests that the tri-block copolymer has a focused chain size distribution. The hydrocarbon tail of the CTA was then removed, and the de-alkylated HPBD-b-$(P4VP)_2$ was converted to the amphiphilic tri-block copolymer HPBD-$(P4MVP)_2$, its NMR spectrum is shown in FIG. 7B. When proton a was set to 110, there were 165 protons from proton c, suggesting all 4VP units have been converted to 4MVP.

Figure 7A:
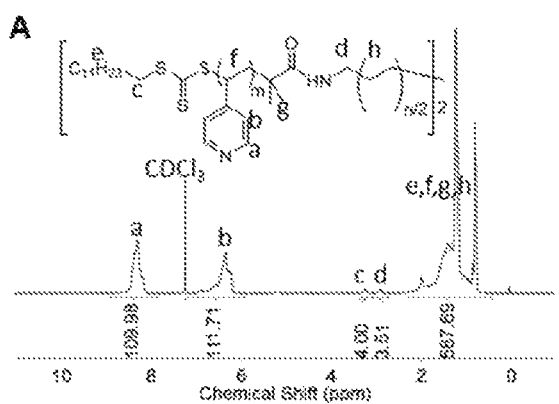
FIGS. 7A and 7B are NMR spectrum of (FIG. 7A) HPBD-b-(P4VP)$_2$ and (FIG. 7B) HPBD-b-(P4MVP)$_2$.
Figure 7B:
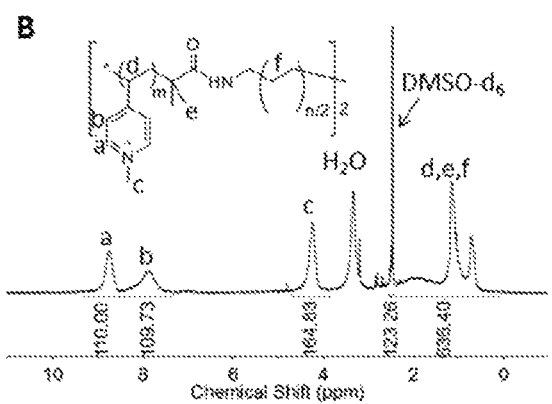

FIGS. 7A and 7B are NMR spectrum of (FIG. 7A) HPBD-b-$(P4VP)_2$ and (FIG. 7B) HPBD-b-$(P4MVP)_2$.

Preparation of polymersomes. Polymersomes were formed by dissolving HPBD-b-$(P4MVP)_2$ in 3/1 (vol. ratio) of DMSO/THF and dialyzed in Millipore water for two days.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112 as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

1. Wallin, E.; von Heijne, G., Genome-wide analysis of integral membrane proteins from eubacterial, archaean, and eukaryotic organisms. Protein Sci. 1998, 7 (4), 1029-38.
2. Stahlberg, H.; Fotiadis, D.; Scheuring, S.; Remigy, H.; Braun, T.; Mitsuoka, K.; Fujiyoshi, Y.; Engel, A., Two-dimensional crystals: a powerful approach to assess structure, function and dynamics of membrane proteins. FEBS Lett. 2001, 504 (3), 166-172.
3. Lee, J. R.; White, T. W., Connexin-26 mutations in deafness and skin disease. Expert reviews in molecular medicine 2009, 11, e35.
4. Orellana, J. A.; Avendano, B. C.; Montero, T. D., Role of connexins and pannexins in ischemic stroke. Curr Med Chem 2014, 21 (19), 2165-82.
5. Schmidt, B. Z.; Haaf, J. B.; Leal, T.; Noel, S., Cystic fibrosis transmembrane conductance regulator modulators in cystic fibrosis: current perspectives. Clin Pharmacol 2016, 8, 127-140.
6. Beyder, A.; Farrugia, G., Ion channelopathies in functional GI disorders. Am J Physiol Gastrointest Liver Physiol 2016, 311 (4), G581-G586.
7. Kumar, P.; Kumar, D.; Jha, S. K.; Jha, N. K.; Ambasta, R. K., Ion Channels in Neurological Disorders. Adv Protein Chem Struct Biol 2016, 103, 97-136.
8. Kuang, L. J.; Fernandes, D. A.; O'Halloran, M.; Zheng, W.; Jiang, Y. J.; Ladizhansky, V.; Brown, L. S.; Liang, H. J., "Frozen" block copolymer nanomembranes with light-driven proton pumping performance. ACS Nano 2014, 8 (1), 537-545.
9. Beales, P. A.; Khan, S.; Muench, S. P.; Jeuken, L. J. C., Durable vesicles for reconstitution of membrane proteins in biotechnology. Biochem. Soc. Trans. 2017, 45, 15-26.
10. Plant, A. L., Supported hybrid bilayer membranes as rugged cell membrane mimics. Langmuir 1999, 15 (15), 5128-5135.
11. Ross, E. E.; Rozanski, L. J.; Spratt, T.; Liu, S. C.; O'Brien, D. F.; Saavedra, S. S., Planar supported lipid bilayer polymers formed by vesicle fusion. 1. Influence of diene monomer structure and polymerization method on film properties. Langmuir 2003, 19 (5), 1752-1765.
12. Daniel, S.; Albertorio, F.; Cremer, P. S., Making lipid membranes rough, tough, and ready to hit the road. MRS Bull. 2006, 31 (7), 536-540.
13. Shim, J. W.; Gu, L. Q., Stochastic sensing on a modular chip containing a single-ion channel. Anal. Chem. 2007, 79 (6), 2207-2213.
14. Ritchie, T. K.; Grinkova, Y. V.; Bayburt, T. H.; Denisov, I. G.; Zolnerciks, J. K.; Atkins, W. M.; Sligar, S. G., Chapter 11—Reconstitution of membrane proteins in phospholipid bilayer nanodiscs. Methods Enzymol. 2009, 464, 211-31.
15. Schuler, M. A.; Denisov, I. G.; Sligar, S. G., Nanodiscs as a new tool to examine lipid-protein interactions. Methods Mol Biol 2013, 974, 415-33.
16. Denisov, I. G.; Sligar, S. G., Nanodiscs for structural and functional studies of membrane proteins. Nat. Struct. Mol. Biol. 2016, 23 (6), 481-6.
17. Denisov, I. G.; Sligari, S. G., Nanodiscs in Membrane Biochemistry and Biophysics. Chem. Rev. 2017, 117 (6), 4669-4713.
18. Jonas, A.; Wald, J. H.; Toohill, K. L. H.; Krul, E. S.; Kezdy, K. E., Apolipoprotein A-I structure and lipid properties in homogeneous, reconstituted spherical and discoidal high-density-lipoproteins. J. Biol. Chem. 1990, 265 (36), 22123-22129.
19. Hagn, F.; Etzkorn, M.; Raschle, T.; Wagner, G., Optimized phospholipid bilayer nanodiscs facilitate high-resolution structure determination of membrane proteins. J. Am. Chem. Soc. 2013, 135 (5), 1919-25.
20. Viegas, A.; Viennet, T.; Etzkorn, M., The power, pitfalls and potential of the nanodisc system for NMR-based studies. Biol Chem 2016.
21. Zoghbi, M. E.; Cooper, R. S.; Altenberg, G. A., The Lipid Bilayer Modulates the Structure and Function of an ATP-binding Cassette Exporter. J. Biol. Chem. 2016, 291 (9), 4453-61.
22. Gao, Y.; Cao, E.; Julius, D.; Cheng, Y., TRPV1 structures in nanodiscs reveal mechanisms of ligand and lipid action. Nature 2016, 534 (7607), 347-51.
23. Burgess, B. L.; He, Y. M.; Baker, M. M.; Luo, B.; Carroll, S. F.; Forte, T. M.; Oda, M. N., NanoDisk containing super aggregated amphotericin B: a high therapeutic index antifungal formulation with enhanced potency. Inter. J. Nanomedicine 2013, 8, 4733-4742.
24. Ryan, R. O., Nanodisks: hydrophobic drug delivery vehicles. Expert Opinion on Drug Delivery 2008, 5 (3), 343-351.
25. Zhang, W. P.; Sun, J.; Liu, Y.; Tao, M. Y.; Ai, X. Y.; Su, X. N.; Cai, C. F.; Tang, Y. L.; Feng, Z.; Yan, X. D.; Chen, G. L.; He, Z. G., PEG-Stabilized Bilayer Nanodisks As Carriers for Doxorubicin Delivery. Molecular Pharmaceutics 2014, 11 (10), 3279-3290.
26. Discher, B. M.; Won, Y. Y.; Ege, D. S.; Lee, J. C. M.; Bates, F. S.; Discher, D. E.; Hammer, D. A., Polymersomes: Tough vesicles made from diblock copolymers. Science 1999, 284 (5417), 1143-1146.
27. Discher, D. E.; Eisenberg, A., Polymer vesicles. Science 2002, 297 (5583), 967-973.
28. Meier, W.; Nardin, C.; Winterhalter, M., Reconstitution of channel proteins in (polymerized) ABA triblock copolymer membranes. Angew. Chem. Int. Ed. 2000, 39 (24), 4599-4602.
29. Nardin, C.; Thoeni, S.; Widmer, J.; Winterhalter, M.; Meier, W., Nanoreactors based on (polymerized) ABA-triblock copolymer vesicles. Chem. Commun. 2000, (15), 1433-1434.
30. Kumar, M.; Grzelakowski, M.; Zilles, J.; Clark, M.; Meier, W., Highly permeable polymeric membranes based on the incorporation of the functional water channel protein Aquaporin Z. Proc. Natl. Acad. Sci. U.S.A 2007, 104 (52), 20719-20724.
31. Kowal, J. L.; Kowal, J. K.; Wu, D.; Stahlberg, H.; Palivan, C. G.; Meier, W. P., Functional surface engineering by nucleotide-modulated potassium channel insertion into polymer membranes attached to solid supports. Biomaterials 2014, 35 (26), 7286-7294.
32. Itel, F.; Najer, A.; Palivan, C. G.; Meier, W., Dynamics of Membrane Proteins within Synthetic Polymer Membranes with Large Hydrophobic Mismatch. Nano Lett. 2015, 15 (6), 3871-3878.

33. Hua, D. B.; Kuang, L. J.; Liang, H. J., Self-directed reconstitution of proteorhodopsin with amphiphilic block copolymers induces the formation of hierarchically ordered proteopolymer membrane arrays. J. Am. Chem. Soc. 2011, 133, 2354-2357.
34. Kuang, L. J.; Olson, T. L.; Lin, S.; Flores, M.; Jiang, Y. J.; Zheng, W.; Williams, J. C.; Allen, J. P.; Liang, H. J., Interface for light-driven electron transfer by photosynthetic complexes across block copolymer membranes. J. Phys. Chem. Lett. 2014, 5 (5), 787-791.
35. Udeep Chawla; Jiang, Y.; Zheng, W.; Kuang, L.; Perera, S. M. D. C.; Pitman, M. C.; Brown, M. F.; Liang, H., A Usual G-Protein-Coupled Receptor in Unusual Membranes. Angew. Chem. 2016, 55, 588-592.
36. Christian, D. A.; Cai, S.; Bowen, D. M.; Kim, Y.; Pajerowski, J. D.; Discher, D. E., Polymersome carriers: From self-assembly to siRNA and protein therapeutics. European Journal of Pharmaceutics and Biopharmaceutics 2009, 71 (3), 463-474.
37. Ranquin, A.; Versees, W.; Meier, W.; Steyaert, J.; Van Gelder, P., Therapeutic nanoreactors: Combining chemistry and biology in a novel triblock copolymer drug delivery system. Nano Lett. 2005, 5 (11), 2220-2224.
38. Shih, A. Y.; Arkhipov, A.; Freddolino, P. L.; Schulten, K., Coarse grained protein-lipid model with application to lipoprotein particles. J. Phys. Chem. B 2006, 110 (8), 3674-3684.
39. Shih, A. Y.; Denisov, I. G.; Phillips, J. C.; Sligar, S. G.; Schulten, K., Molecular dynamics simulations of discoidal bilayers assembled from truncated human lipoproteins. Biophys. J. 2005, 88 (1), 548-556.
40. Doerrler, W. T.; Raetz, C. R., ATPase activity of the MsbA lipid flippase of Escherichia coli. J. Biol. Chem. 2002, 277 (39), 36697-705.
41. Doerrler, W. T.; Gibbons, H. S.; Raetz, C. R., MsbA-dependent translocation of lipids across the inner membrane of Escherichia coli. J. Biol. Chem. 2004, 279 (43), 45102-9.
42. Cooper, R. S.; Altenberg, G. A., Association/dissociation of the nucleotide-binding domains of the ATP-binding cassette protein MsbA measured during continuous hydrolysis. J. Biol. Chem. 2013, 288 (29), 20785-96.
43. Valiyaveetil, F. I.; Zhou, Y. F.; Mackinnon, R., Lipids in the structure, folding, and function of the KcsA K+ channel. Biochemistry 2002, 41 (35), 10771-10777.
44. Alvis, S. J.; Williamson, I. M.; East, J. M.; Lee, A. G., Interactions of anionic phospholipids and phosphatidylethanolamine with the potassium channel KcsA. Biophys. J. 2003, 85 (6), 3828-3838.
45. Opekarova, M.; Tanner, W., Specific lipid requirements of membrane proteins—a putative bottleneck in heterologous expression. Biochim. Biophys. Acta, Biomembr. 2003, 1610 (1), 11-22.
46. Soubias, O.; Gawrisch, K., Probing specific lipid-protein interaction by saturation transfer difference NMR spectroscopy. J. Am. Chem. Soc. 2005, 127 (38), 13110-13111.
47. Mitchell, D. C.; Lawrence, J. T. R.; Litman, B. J., Primary alcohols modulate the activation of the G protein-coupled receptor rhodopsin by a lipid-mediated mechanism. J. Biol. Chem. 1996, 271 (32), 19033-19036.
48. Cantor, R. S., Lipid composition and the lateral pressure profile in bilayers. Biophys. J. 1999, 76 (5), 2625-2639.
49. Andersen, O. S.; Koeppe, R. E., Bilayer thickness and membrane protein function: An energetic perspective. Annu. Rev. Biophys. Biomol. Struct. 2007, 36, 107-130.
50. Phillips, R.; Ursell, T.; Wiggins, P.; Sens, P., Emerging roles for lipids in shaping membrane-protein function. Nature 2009, 459 (7245), 379-385.
51. Brown, M. F., Curvature forces in membrane lipid-protein interactions. Biochemistry 2012, 51 (49), 9782-9795.
52. Lee, A. G., Lipid-protein interactions in biological membranes: a structural perspective. Biochim. Biophys. Acta, Biomembr. 2003, 1612 (1), 1-40.
53. Marsh, D.; Horvath, L. I., Structure, dynamics and composition of the lipid-protein interface. Perspectives from spin-labelling. Biochimica Et Biophysica Acta-Reviews on Biomembranes 1998, 1376 (3), 267-296.
54. Soubias, O.; Gawrisch, K., The role of the lipid matrix for structure and function of the GPCR rhodopsin. Biochim. Biophys. Acta, Biomembr. 2012, 1818 (2), 234-240.
55. Reimhult, E.; Kumar, K., Membrane biosensor platforms using nano- and microporous supports. Trends Biotechnol. 2008, 26 (2), 82-89.
56. Curnow, P., Membrane proteins in nanotechnology. Biochem. Soc. Trans. 2009, 37, 643-652.
57. Khan, S.; Li, M. Q.; Muench, S. P.; Jeuken, L. J. C.; Beales, P. A., Durable proteo-hybrid vesicles for the extended functional lifetime of membrane proteins in bionanotechnology. Chem. Commun. 2016, 52 (73), 11020-11023.
58. Kowal, J.; Wu, D. L.; Mikhalevich, V.; Palivan, C. G.; Meier, W., Hybrid Polymer-Lipid Films as Platforms for Directed Membrane Protein Insertion. Langmuir 2015, 31 (17), 4868-4877.
59. Bao, H.; Dalal, K.; Wang, V.; Rouiller, I.; Duong, F., The maltose ABC transporter: Action of membrane lipids on the transporter stability, coupling and ATPase activity. Biochim. Biophys. Acta, Biomembr. 2013, 1828 (8), 1723-1730.
60. McClary, W. D.; Sumida, J. P.; Scian, M.; Paco, L.; Atkins, W. M., Membrane Fluidity Modulates Thermal Stability and Ligand Binding of Cytochrome P4503A4 in Lipid Nanodiscs. Biochemistry 2016, 55 (45), 6258-6268.
61. Wadsater, M.; Maric, S.; Simonsen, J. B.; Mortensen, K.; Cardenas, M., The effect of using binary mixtures of zwitterionic and charged lipids on nanodisc formation and stability. Soft Matter 2013, 9 (7), 2329-2337.
62. Fiori, M. C.; Krishnan, S.; Cortes, D. M.; Retamal, M. A.; Reuss, L.; Altenberg, G. A.; Cuello, L. G., Functional hemichannels formed by human connexin 26 expressed in bacteria. Biosci. Rep. 2015, 35 (2).
63. Bai, J.; Swartz, D. J.; Protasevich, I I; Brouillette, C. G.; Harrell, P. M.; Hildebrandt, E.; Gasser, B.; Mattanovich, D.; Ward, A.; Chang, G.; Urbatsch, I. L., A gene optimization strategy that enhances production of fully functional P-glycoprotein in Pichia pastoris. PLoS One 2011, 6 (8), e22577.
64. Booth, D. S.; Avila-Sakar, A.; Cheng, Y. F., Visualizing Proteins and Macromolecular Complexes by Negative Stain EM: from Grid Preparation to Image Acquisition. J. Vis. Exp. 2011, (58).
65. Rohou, A.; Grigorieff, N., CTFFIND4: Fast and accurate defocus estimation from electron micrographs. J. Struct. Biol. 2015, 192 (2), 216-221.
66. Tang, G.; Peng, L.; Baldwin, P. R.; Mann, D. S.; Jiang, W.; Rees, I.; Ludtke, S. J., EMAN2: An extensible image processing suite for electron microscopy. J. Struct. Biol. 2007, 157 (1), 38-46.

The invention claimed is:

1. A nanoscale discoidal membrane comprising:
   an amphiphilic membrane patch comprising self-assembled molecular amphiphiles comprising randomly polymerized styrene-maleic acid derivative repeating units that carry zero or nearly zero negative charges capable of supporting one or more membrane proteins in the amphiphilic membrane patch; and
   one or more amphipathic scaffold macromolecules that encase the nanoscale discoidal membrane.

2. The nanoscale discoidal membrane of claim 1, further comprising one or more membrane proteins in the amphiphilic membrane patch.

3. The nanoscale discoidal membrane of claim 1, wherein the membrane proteins stabilized in the amphiphilic membrane have a higher mechanical and chemical stability when compared to the same membrane protein in a liposome.

4. The nanoscale discoidal membrane of claim 1, wherein the one or more membrane proteins are soluble at a pH<7.0 or are soluble in the presence of cations and a pH<7.0.

5. The nanoscale discoidal membrane of claim 1, further comprising one or more membrane proteins adapted for the determination of acidification-induced rhodopsins spectral shifts, activation of ion channels, or measurement of ATPases.

6. The nanoscale discoidal membrane of claim 1, wherein the one or more membrane proteins are rhodopsins, ion pumps, integral membrane proteins, are proteins soluble in the presence of cations, are at least one of P-type, F-type, V-type, or ABC ATPases, or ATP-binding cassette proteins.

7. The nanoscale discoidal membrane of claim 1, wherein the amphiphiles comprise lipids isolated from cell, synthetic lipids, or amphiphilic block copolymers.

8. The nanoscale discoidal membrane of claim 1, wherein the one or more membrane proteins shows minimal or no structural change upon storage at 4° C. or 20° C.

9. The nanoscale discoidal membrane of claim 1, wherein the amphiphilic block copolymer has the formula:

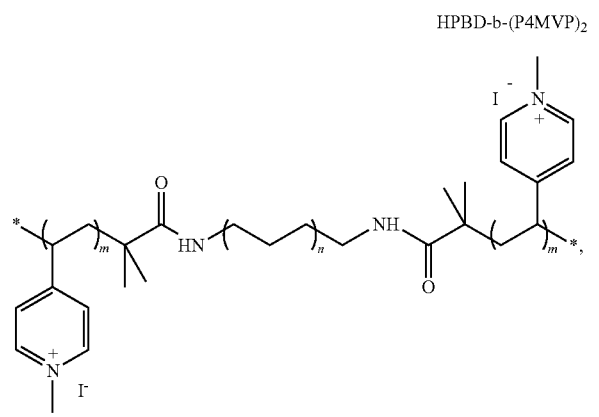

HPBD-b-(P4MVP)$_2$ wherein n is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 140, 145, 150, 155, 160, 165, 170, 175, 185, 190, 195, 200, or more, and m is 1 to 100.

10. The nanoscale discoidal membrane of claim 1, wherein the amphipathic scaffold macromolecule comprises randomly polymerized styrene-maleic acid derivative repeating units that carry zero or nearly zero negative charges are the zwitterionic styrene-maleic acid polymers (zSMAs) with the structure:

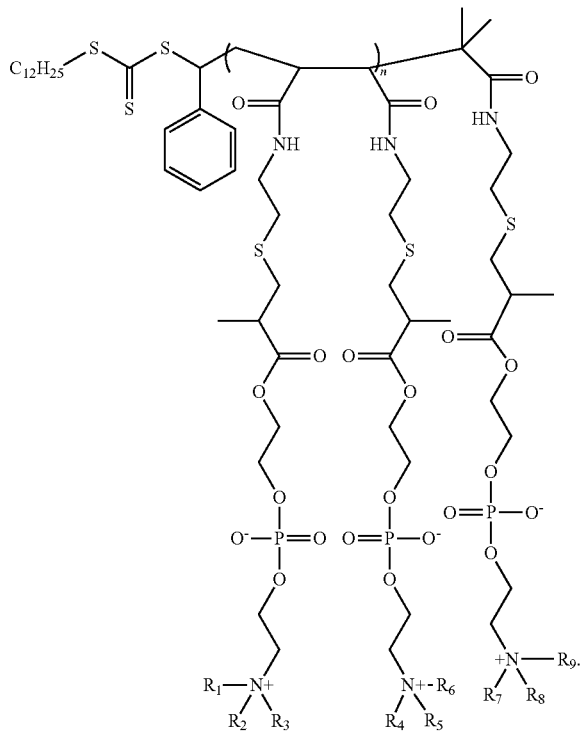

11. The amphipathic scaffold macromolecules of claim 10, wherein $R_1$, $R_2$, $R_3$, $R_4$, $R_5$, $R_6$, $R_7$, $R_8$, $R_9$ are selected from hydrogen; deuterium; a halogen group; a nitrile group; a nitro group; an imide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group including one or more of N, O, or S atoms; and wherein n is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 140, 145, 150, 155, 160, 165, 170, 175, 185, 190, 195, 200, or more.

12. The amphipathic scaffold macromolecules of claim 11, wherein the end groups of zSMA (e.g. $C_{12}H_{25}$—S—(C=S)—S—) is introduced by reversible addition-fragmentation chain-transfer (RAFT) polymerization using S-1-dodecyl-S'-(α,α'-dimethyl-α"-acetic acid)trithiocarbonate (DATC) as the chain transfer agent or wherein zSMA is cleaved or converted to other groups by anionic polymerization, cationic polymerization, conventional free radical polymerization, or other types of controlled/living free radical polymerization such as atom transfer radical polymerization (ATRP), or nitroxide mediated polymerization (NMP).

13. A nanodisc comprising an amphiphilic block copolymer membrane patch comprising randomly polymerized styrene-maleic acid derivative repeating units that carry zero or nearly zero negative charges, wherein the amphiphilic block copolymer membrane patch is comprised of a hydrophobic membrane-forming and hydrophilic membrane-surface blocks encased within one or more amphipathic scaffold macromolecules capable of stabilizing one or more membrane proteins.

14. The nanodisc of claim 13, wherein the one or more membrane proteins are soluble at a pH<7.0.

15. The nanodisc of claim 13, wherein the one or more membrane proteins are adapted for the determination of acidification-induced rhodopsins spectral shifts, activation of ion channels, or measurement of ATPases.

16. The nanodisc of claim 13, wherein the one or more membrane proteins are rhodopsins, ion pumps, integral membrane proteins, are proteins soluble in the presence of cations, are at least one of P-type, F-type, V-type, or ABC ATPases, or ATP-binding cassette proteins.

17. The nanodisc of claim 13, wherein the one or more membrane proteins are soluble in the presence of cations and a pH<7.0.

18. The nanoscale discoidal membrane of claim 13, wherein the amphiphilic block copolymer has the formula:

HPBD-b-(P4MVP)$_2$ wherein n is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 140, 145, 150, 155, 160, 165, 170, 175, 185, 190, 195, 200, or more, and m is 1 to 100.

19. The nanoscale discoidal membrane of claim 13, wherein the amphipathic scaffold macromolecule comprises randomly polymerized styrene-maleic acid derivative repeating units that carry zero or nearly zero negative charges are the zwitterionic styrene-maleic acid polymers (zSMAs) with the structure:

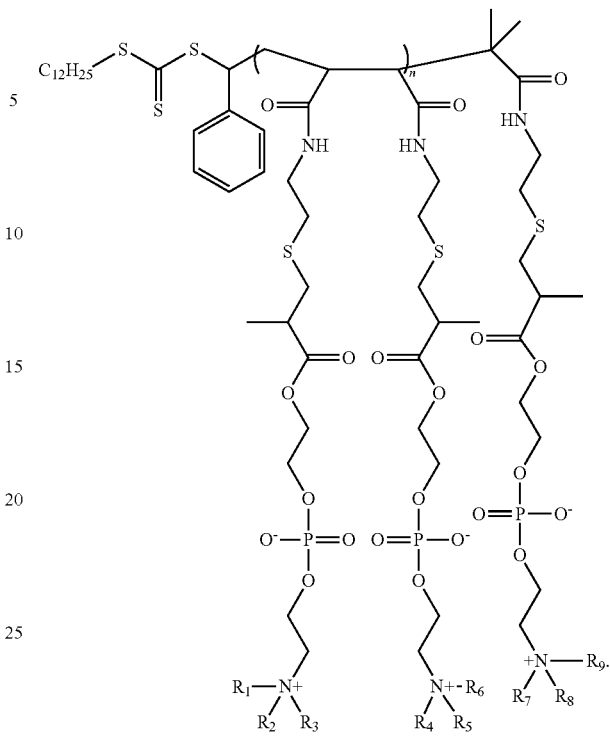

20. The amphipathic scaffold macromolecules of claim 19, wherein $R_1$, $R_2$, $R_3$, $R_4$, $R_5$, $R_6$, $R_7$, $R_8$, $R_9$ are selected from hydrogen; deuterium; a halogen group; a nitrile group; a nitro group; an imide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group including one or more of N, O, or S atoms; and wherein n is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 140, 145, 150, 155, 160, 165, 170, 175, 185, 190, 195, 200, or more.

21. The amphipathic scaffold macromolecules of claim 20, wherein the end groups of zSMA is introduced by reversible addition-fragmentation chain-transfer (RAFT) polymerization using S-1-dodecyl-S'-(α,α'-dimethyl-α"-acetic acid)trithiocarbonate (DATC) as the chain transfer agent or wherein zSMA is cleaved or converted to other groups by anionic polymerization, cationic polymerization, conventional free radical polymerization, atom transfer radical polymerization (ATRP), or nitroxide mediated polymerization (NMP).

* * * * *